US012702495B2

(12) United States Patent
Colbrunn et al.

(10) Patent No.: US 12,702,495 B2
(45) Date of Patent: *Aug. 11, 2026

(54) DETECTION OF UNINTENTIONAL MOVEMENT OF A REFERENCE MARKER AND AUTOMATIC RE-REGISTRATION

(71) Applicant: THE CLEVELAND CLINIC FOUNDATION, Cleveland, OH (US)

(72) Inventors: Robb Colbrunn, Hinckley, OH (US); Callan Gillespie, Cleveland, OH (US); Joshua Golubovsky, Cleveland, OH (US)

(73) Assignee: THE CLEVELAND CLINIC FOUNDATION, Cleveland, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 19/061,409

(22) Filed: Feb. 24, 2025

(65) Prior Publication Data

US 2025/0318878 A1 Oct. 16, 2025

Related U.S. Application Data

(63) Continuation of application No. 18/107,349, filed on Feb. 8, 2023, now Pat. No. 12,279,834.

(Continued)

(51) Int. Cl.

*A61B 34/20* (2016.01)
*A61B 34/32* (2016.01)

(Continued)

(52) U.S. Cl.

CPC .............. *A61B 34/20* (2016.02); *A61B 34/32* (2016.02); *A61B 90/03* (2016.02); *A61B 90/39* (2016.02);

(Continued)

(58) Field of Classification Search

CPC ......... A61B 34/20; A61B 34/32; A61B 90/03; A61B 90/39; A61B 2034/302;

(Continued)

(56) References Cited

U.S. PATENT DOCUMENTS 10,512,508 B2 * 12/2019 Rohling ............... H04N 13/254
2016/0022374 A1 * 1/2016 Haider ................. A61B 17/142 606/96

(Continued)

*Primary Examiner* — Sihar A Karwan

(74) *Attorney, Agent, or Firm* — Tarolli, Sundheim, Covell & Tummino LLP

(57) ABSTRACT

Described herein is the automatic re-registration of a bumped reference marker, where the navigation system includes the reference marker, a bump detection sensor(s), and a computing device. The computing device can store positional relationships between the reference marker, the bump detection sensor(s), and the anatomy from an initial image registration and receive position data of the reference marker and bump detection sensor(s) at times during use. The computing device can determine a delta matrix based on the stored and received information and then determine if the reference marker has been bumped. If the reference marker has been bumped the computing device can determine if automatic re-registration is required and complete the automatic re-registration if needed to correct for the bump.

20 Claims, 14 Drawing Sheets

Related U.S. Application Data

(60) Provisional application No. 63/307,665, filed on Feb. 8, 2022.

(51) Int. Cl.

| | |
|---|---|
| ***A61B 90/00*** | (2016.01) |
| ***B25J 9/16*** | (2006.01) |
| *A61B 34/30* | (2016.01) |

(52) U.S. Cl.

CPC ....... *B25J 9/1664* (2013.01); *A61B 2034/302* (2016.02); *A61B 2090/036* (2016.02); *A61B 2090/3983* (2016.02)

(58) Field of Classification Search

CPC ...... A61B 2090/036; A61B 2090/3983; A61B 2017/00119; A61B 34/30; A61B 2034/2048; A61B 2034/2055; B25J 9/1664; B25J 9/1689

See application file for complete search history.

(56) References Cited

U.S. PATENT DOCUMENTS

| | | | | |
|---|---|---|---|---|
| 2016/0256223 | A1* | 9/2016 | Haimerl | A61B 34/20 |
| 2017/0069073 | A1* | 3/2017 | Sela | A61B 90/39 |
| 2018/0185113 | A1* | 7/2018 | Gregerson | A61B 5/055 |
| 2019/0337258 | A1* | 11/2019 | Fukuda | G01B 11/26 |
| 2021/0369355 | A1* | 12/2021 | Masaki | A61B 5/6852 |

* cited by examiner

700

IMAGE REGISTRATION
702

BEGIN SURGICAL PROCEDURE
704

CHECK POSITION OF REFERENCE MARKER AND BUMP DETECTION SENSOR(S) AT A TIME
706

BUMP DETECTED DURING SURGICAL PROCEDURE
708

AUTOMATICALLY RE-REGISTER AND, OPTIONALLY, OUTPUT A CORRECTED POSE
710

COMPLETE SURGICAL PROCEDURE
712

PROVIDE A TRAJECTORY TO AN END EFFECTOR OF A STEREOTACTIC SURGICAL ROBOT
1002

DETECT COMPLIANCE AND/OR POSITIONING ERROR IN THE STEREOTACTIC SURGICAL ROBOT
1004

DETERMINE WHETHER AN AUTOMATIC RE-REGISTRATION IS REQUIRED
1006

AUTOMATICALLY RE-REGISTER AND, OPTIONALLY, OUTPUT A CORRECTED POSE
1008

MODIFY THE TRAJECTORY IN RESPONSE TO THE AUTOMATIC RE-REGISTRATION
1010

OUPUT THE MODIFIED TRAJECTORY TO THE END EFFECTOR OF THE STEREOTACTIC SURGICAL ROBOT
1012

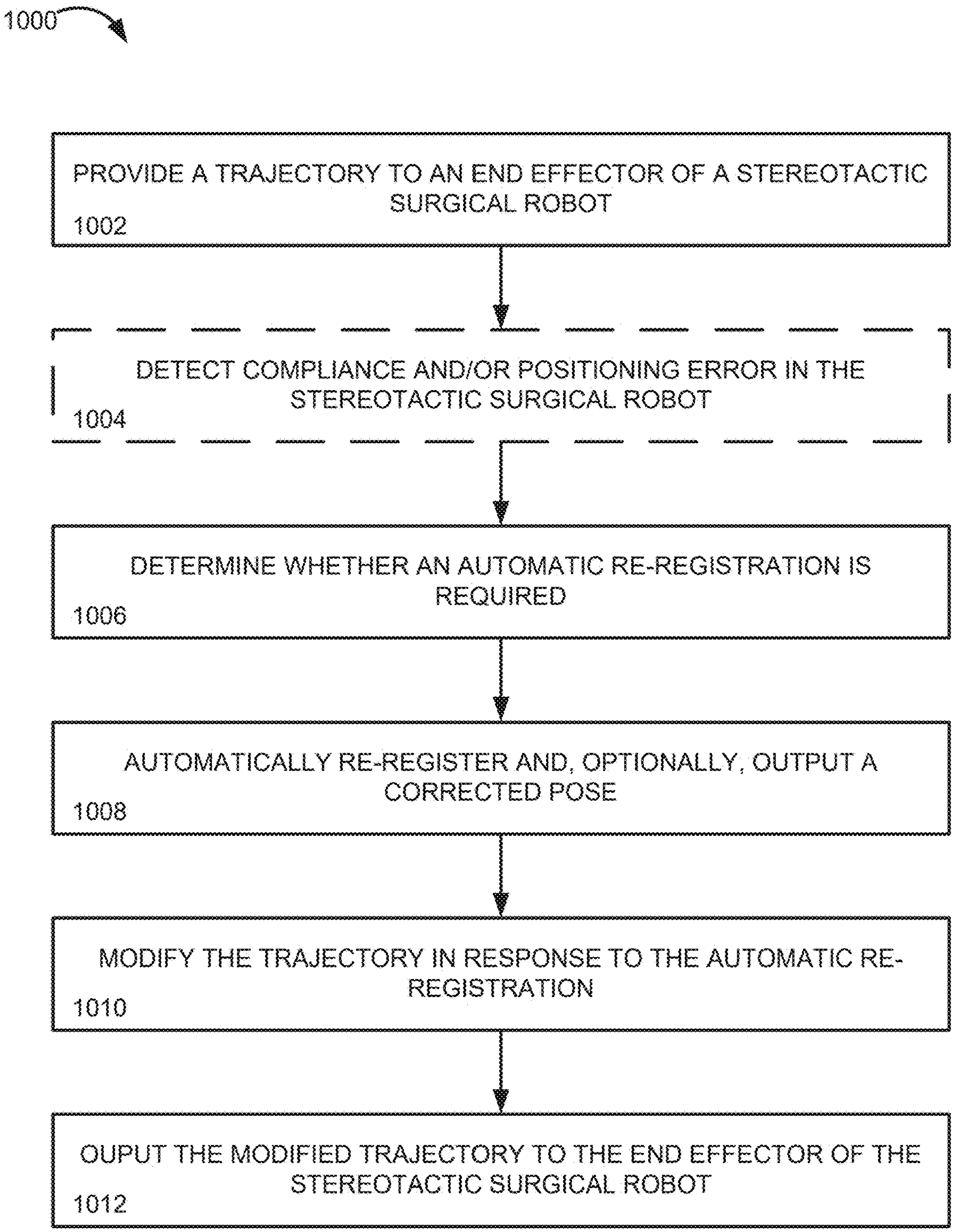

FIG. 10

DETECTION OF UNINTENTIONAL MOVEMENT OF A REFERENCE MARKER AND AUTOMATIC RE-REGISTRATION

CROSS-REFERENCE TO RELATED APPLICATIONS

This application is a Continuation of U.S. patent application Ser. No. 18/107,349, filed 8 Feb. 2023, which claims the benefit of U.S. Provisional Application No. 63/307,665, filed 8 Feb. 2022, entitled REFERENCE ARRAY BUMP DETECTION AND AUTOMATIC RE-REGISTRATION SYSTEM FOR INTRAOPERATIVE NAVIGATION IN SPINE SURGERY, all of which are incorporated herein by reference in its entirety.

TECHNICAL FIELD

The present disclosure relates generally to an intraoperative navigation system for and, more specifically, to systems and methods for intraoperative navigation that can detect unintentional movement of a reference marker and automatic re-registration of the reference marker.

BACKGROUND

Current intraoperative navigation and image guided surgery systems for spinal surgery require a reference marker to be placed on the patient's spine and a CT scan to be taken of the patient to register the anatomy with the reference marker. In this way, the surgeon/surgical team can know where their tools are with respect to the anatomy at all times and ensure holes and cuts are properly placed while avoiding sensitive structures such as the spinal cord and roots. Other surgical procedures utilize reference markers in similar ways. Unfortunately, the reference marker can be accidentally bumped or otherwise unintentionally moved throughout the surgical procedure. With current spine navigation systems, if the reference marker is bumped and the bump is noticed by the surgeon/surgical team or other personnel, then another CT scan must be performed to reregister the marker to the anatomy, exposing the patient, and often at least a portion of the surgical team as well, to additional radiation, as well as prolonging the operative time. Moreover, if the reference marker is bumped and moved without being detected, the surgeon/surgical team may proceed with the surgical procedure, potentially causing surgical complications and negatively impacting patient outcomes.

SUMMARY

The present disclosure provides systems and methods that can detect unintentional movement of a reference marker and automatically re-register the reference marker, eliminating at least the additional radiation from another image registration, prolonged operative time, and surgical complications/negative patient outcomes.

In one aspect, the present disclosure includes a navigation system comprising a reference marker, at least one bump detection sensor, and a computing device. The reference marker is detectable by an image acquisition device and configured to be positioned on a portion of a patient's anatomy. The at least one bump detection sensor has a lower profile than the reference marker. The reference marker, the at least one bump detection sensor, and the portion of the patient's anatomy are image registered at an initial image registration time. The computing device comprises a memory storing instructions and data, including a static relationship between a position of the at least one bump detection senser and a position of the reference marker at the initial image registration time and a static relationship between the position of the reference marker and a position of the portion of the patient's anatomy at the initial image registration time; and a processor configured to access the memory to execute the instructions. The instructions can include: receive position data of an actual position of the reference marker at a time; receive position data of an actual position of each of the at least one bump detection sensor at the time; determine a delta matrix based on the position data of the actual position of the reference marker at the time, the position data of the actual position of each of the at least one bump detect sensor at the time, and the static relationship between the positions of the at least one bump detection senser and the reference marker at the initial image registration time; determine the shift in the actual position of the reference marker relative to the position of the anatomy at the time based on the delta matrix and the static relationship between the positions of the reference marker and the portion of the patient's anatomy at the initial image registration time; and determine whether automatic re-registration is required based on one or more predefined thresholds.

In another aspect, the present disclosure includes a method for correcting for a bump of a reference marker including the following steps. Receiving, by a computing device comprising a processor, positional information about a reference marker detectable by an image acquisition device and positioned on a portion of a patient's anatomy and at least one bump detection sensor having a lower profile than the reference marker. Where the reference marker, the at least one bump detection sensor, and the portion of the patient's anatomy are image registered at an initial image registration time. And where the positional information comprises: a static relationship between a position of the at least one bump detection senser and a position of the reference marker at the initial image registration time, a static relationship between the position of the reference marker and a position of the portion of the patient's anatomy at the initial image registration time, position data of an actual position of the reference marker at a time, and position data of an actual position of each of the at least one bump detection sensor at the time. Determining, by the computing device, a delta matrix based on the position data of the actual position of the reference marker at the time, the position data of the actual position of each of the at least one bump detect sensor at the time, and the static relationship between the positions of the at least one bump detection senser and the reference marker at the initial image registration time. Determining, by the computing device, the shift in the actual position of the reference marker relative to the position of the anatomy at the time based on the delta matrix and the static relationship between the positions of the reference marker and the portion of the patient's anatomy at the initial image registration time. And, determining, by the computing device, whether automatic re-registration is required based on one or more predefined thresholds.

BRIEF DESCRIPTION OF THE DRAWINGS

The foregoing and other features of the present disclosure will become apparent to those skilled in the art to which the present disclosure relates upon reading the following description with reference to the accompanying drawings, in which:

FIG. 10 is a process flow diagram illustrating methods for bump detection and automatic re-registration for implementation with a stereotactic surgical robot;

DETAILED DESCRIPTION

I. Definitions

Figure 1:
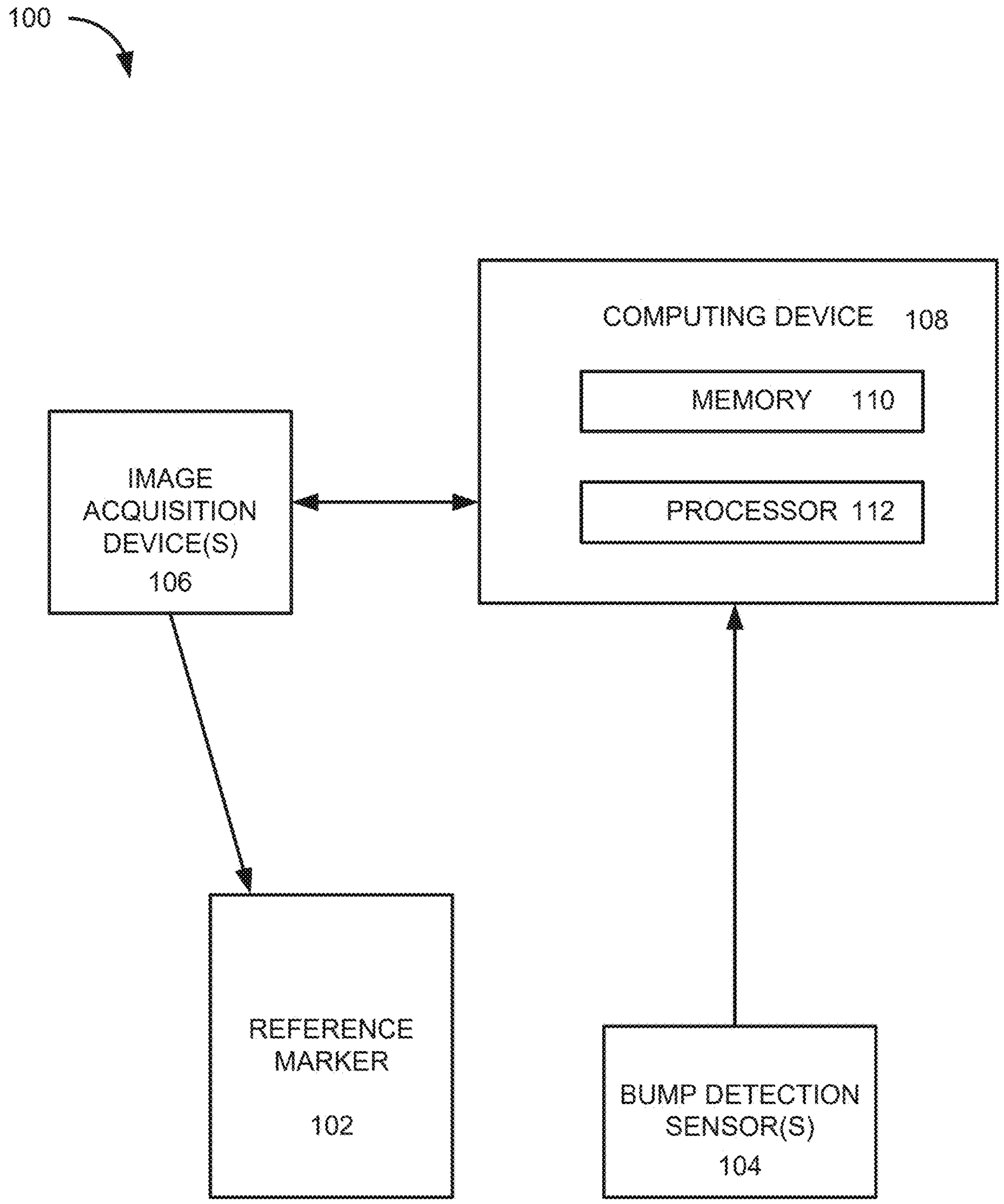
FIG. 1 is a diagram illustrating a navigation system designed to provide bump detection and automatic re-registration.

In the context of the present disclosure, the singular forms "a," "an", and "the" can also include the plural forms, unless the context clearly indicates otherwise.

The terms "comprises" and/or "comprising," as used herein, can specify the presence of stated features, steps, operations, elements, and/or components, but do not preclude the presence or addition of one or more other features, steps, operations, elements, components, and/or groups.

As used herein, the term "and/or" can include any and all combinations of one or more of the associated listed items.

Additionally, although the terms "first," "second," etc. may be used herein to describe various elements, these elements should not be limited by these terms. These terms are only used to distinguish one element from another. Thus, a "first" element discussed below could also be termed a "second" element without departing from the teachings of the present disclosure. The sequence of operations (or acts/steps) is not limited to the order presented in the claims or figures unless specifically indicated otherwise.

As used herein, the term "surgical procedure" refers to an invasive medical procedure performed on a patient using at least one instrument. One example of a surgical procedure is an operation, which involves cutting of one or more of a person's tissues, closure of a previously sustained wound, and/or the use of common surgical settings or instrumentation (e.g., use of a sterile environment, anesthesia, antiseptic conditions, typical surgical instruments, and suturing or stapling). A surgical procedure can also include pre- and post-operative care of the patient. Generally, a surgical procedure is performed by a surgical team comprising at least a surgeon, a surgeon's assistant, an anesthesiologist, a circulating nurse, and a surgical technologist. Examples of different surgeries include spinal surgery, orthopedic surgery, brain surgery, cardiorespiratory surgery, and the like.

As used herein, the term "navigation system" refers to a computerized technology that allows a surgical team to precisely track a position of at least one instrument being used during a surgical procedure based on at least one reference marker (theoretically in a fixed position). Many navigation systems are "image based" navigation systems, in which the position of the instrument can be tracked by an image capture device and projected onto preoperative imaging data of the anatomy of the patient during a surgical procedure based on a registration of the anatomy and the reference markers during the preoperative imaging. Navigation systems can be included in many different types of technology assisted surgical procedures such as, but not limited to, stereotactic surgery, image guided surgical navigation, computer assisted surgery, navigated surgery, stereotactic navigation, or the like.

As used herein, the term "reference marker" refers to something that is placed at a known location that is assumed to be stationary relative to patient anatomy. The reference marker can be an indicator for an image-based navigation system that is assumed to be stationarily disposed relative to portion of a patient's anatomy and is used to determine the spatial relationships between the patient's anatomy and any tools used in the field of view of the image-based navigation system. A reference marker may also be called a fiducial marker or fiducial and is an object placed in the field of view of an image-based navigation system that appears in the image produced, for use as a point of reference.

As used herein, the terms "unintentional movement", "bump", and "shift" may be used interchangeably and refer to an unintended change in a position, direction, attitude, and/or orientation of an object (e.g., a reference marker) or, in some instances, the act of causing the unintended change in the position, direction, attitude, and/or orientation of the object. For example, a reference marker can be bumped by a member of a surgical team, a piece of equipment (such as tubing), or the like.

As used herein, the term "position" is used interchangeably with "pose" and can refer to linear position and/or rotational orientation.

As used herein, the term "bump detection sensor" refers to a position sensor that can be used to detect an unintentional movement of the reference marker and has a lower physical profile than the reference marker that is less likely to be bumped relative to the anatomy. It should be noted that bump detection sensors can be any type of position sensor, preferably sensing position using non-optical mechanisms (e.g., using mechanisms other than vision based/imaging sensing technologies such as motion capture). Nonlimiting examples include inertial measurement units (IMU) that are based on accelerometers, gyroscopes, and magnetometers, potentiometers, Hall effect sensors, linear variable displacement transducers, strain gauges on flexible substrates, ultrasonic sensors, electromagnetic sensors, and laser distance measurement sensors. As an example, one or more bump detection sensors can be used together with a single reference marker.

As used herein, the term "anatomy" refers to at least a portion of a patient's (e.g., a human, an animal, or another living organism) body undergoing a surgical procedure. A patient's anatomy can refer to, for example, a spine, a portion of a spine such as a spinal process, an arm, a finger, a leg, a tibia, or the like. Anatomy can include rigid bodies and/or non-rigid bodies.

As used herein, the term "rigid body" refers to a solid body in which deformation is zero or so small it can be considered negligible when under the action of at least one external force. The distance between any two given points on a rigid body remains constant in time regardless of external forces or moments exerted on it. A rigid body is usually considered as a continuous distribution of mass. A rigid body can have a linear position and an angular position (also known as orientation, or attitude). An example of an anatomic rigid body is a spinal process or a bone such as the femur, tibia, radius, ulna, or the like.

As used herein, the terms "non-rigid body", "compliant body", or the like can be used interchangeably to refer to something that is more than negligibly deformable. As an example, a non-rigid body can stretch, compress, or bend when subjected to one or more forces. Non-limiting examples of non-rigid bodies include fabric, skin, muscle, the spine as a whole (even though parts are considered rigid), and fat.

As used herein, the term "image registration" refers to an initial step for use of a surgical procedure using a navigation system, where a patient's diagnostic images, such as CT or MR scans, that include at least the portion of the patient's anatomy to be operated on and the reference marker are uploaded into the navigation system to create a 2D or 3D model of the patient's anatomy relative to the reference marker. The 2D or 3D model is used to create a virtual map that is meant to mimic the alignments of the physical anatomy for surgical planning, stereotactic robotic navigation, or the like

II. Overview

Unintentional movement of a reference marker compared to the reference marker's initial, registered position is an issue that is commonly encountered during surgeries where intraoperative navigation is utilized, such as image guided surgeries and stereotactic surgeries. For example, intraoperative navigation is becoming increasingly commonplace in spine surgery where instrumentation is placed, such as during lumbar fusion where screws and rods are implanted into the spine. Current intraoperative spinal navigation technology requires the reference marker to be securely positioned on a rigid portion of the patient's spine on a level above which any work is done on the spine (e.g., if work is done on the L2-L5 levels, then the reference marker is placed on the spinal process at L1) and an intraoperative CT scan is taken of the patient with the reference marker in place such that a reference frame can be created relative to the reference marker. Similar steps are taken for other surgeries using intraoperative navigation to limit the potential for movement of the reference marker throughout the surgical procedure. The CT scan is uploaded to the navigation system after acquisition and individual surgical instruments can be detected and registered by the navigation system relative to the anatomy as shown by the CT scan. The relationship of all instruments used during the surgical procedures to the anatomy relies entirely on the position of the reference marker. Unfortunately, the reference marker can be accidentally bumped during a surgical procedure, for example, by a surgeon's hand, an instrument, or by being caught in a tangle of a suction tubing to name a few.

Currently, if the reference marker is bumped and the bump is noticed by the surgeon or the surgical team, the only option is to reposition the reference marker and take another CT scan, exposing the patient to additional radiation and prolonging the operative time. However, if the reference marker is bumped and not noticed, then the surgical team may proceed with the surgical procedure if the surgical team is not cautious to constantly re-confirm intraoperative anatomy with the navigation system causing surgical complications and negatively impacting patient outcomes. Examples of surgical complications and negative patient outcomes due to a reference marker being inadvertently bumped include improperly placed screws that have breached the pedicle and caused fractures and/or injury to nerve roots, or penetrate the spinal canal and lead to weakness, pain, or paralysis in very severe cases due to faulty navigation. Beyond potential patient harm, current systems can also be cumbersome to employ and significantly increase operation times because surgeons have to frequently re-confirm that the navigation system aligns with their own view of the patient's anatomy before performing an important step in the surgical procedure.

In order to combat the issues caused by a reference marker being unintentionally moved (e.g., accidentally bumped) a novel navigation system, and method of use, for intraoperative use has been designed. The system can detect when the reference marker is bumped and depending on the size of the shift in the position and/or orientation of the reference marker compared to the original position and/or orientation of the reference marker at initial registration can automatically re-register the reference marker, without further imaging required. The automatic re-registration can be based on the shift in the reference marker relative to the registered position of the reference marker and/or a shift in another coordinate system such as a shift in where the bump detection sensor measures a portion of anatomy to be versus where the reference marker measures the portion of the anatomy to be. The navigation system can include the reference marker and at least one other sensor, which is the bump detection sensor(s), that measure the positions and/or orientations used to calculate the shift. Use of the system will reduce potential radiation exposure for both the surgical team and the patient, reduce operative time during the surgical procedure by decreasing the need to manually re-check registration or re-do image registration with additional CT scans. And decrease the risk of neurological, musculoskeletal, or vascular injury to the patient due to incorrect surgical positioning.

III. Navigation System

One aspect of the present disclosure can include a navigation system that can be used when performing surgical procedures such as, but not limited to, image guided surgery (e.g., neurosurgery, orthopedic surgery, urology related surgeries, or the like) or stereotactic surgery (e.g., brain surgeries, stereotactic radiosurgery, ablation, biopsy, or the like). The navigation system can determine when a reference marker used during the surgical procedure experiences an unwanted movement, referred to herein colloquially as a bump, from an initial registered position. The navigation system can also determine if automatic re-registration is required when a bump is detected and when needed automatically re-register the reference marker so the surgical procedure can proceed. The navigation system can decrease the risk of injury to the patient, decrease the time a surgical procedure takes, and can decrease the amount of radiation exposure of the patient and the surgical team.

As shown in FIG. 1, the navigation system 100 can include a reference marker 102 and at least one bump detection sensor 104 (e.g., bump detection sensor(s)). The reference marker 102 can be detectable by at least one image acquisition device 106 (e.g., image acquisition device(s)) that is in wired and/or wireless communication with a computing device 108. The bump detection sensor(s) 104 can also be in wired and/or wireless communication with the computing device 108. Each element of the navigation system 100 may have additional components (e.g., to aid in the coupling or other functions described herein) that are not illustrated. The navigation system can also include the computing device 108, which can include at least a non-transitory memory (e.g., memory 110) for storing instructions and data and a processor 112 for accessing the memory and executing the instructions. While not shown in FIG. 1, the reference marker 102 can be positioned on a portion of a patient's anatomy, which can be a rigid body. The reference marker 102, the bump detection sensor(s) 104, and the portion of the patient's anatomy can be image registered at an initial image registration time by a CT scan or an MR scan. The CT or MR machine can be one of the image acquisition device(s) 106 or can be a separate device. The bump detection sensor(s) 104 can be positioned on the portion of the anatomy, which can be a rigid body, adjacent to the reference marker 102 and can be visible during the initial image registration (but need not be visible during the initial image registration). If more than one bump detection sensor 104 is used, then the first bump detection sensor can be adjacent the reference marker 102 and the other bump detection sensors can be positioned at other locations, such as other locations on the patient, the surgical table, a surgical tool, a stereotactic robot, or the like.

The reference marker 102 can be a marker (of any known type, shape, size, and/or configuration) detectable by image acquisition device(s) 106 and that can be positioned on a portion of a patient's anatomy, which can be a rigid body. The reference marker 102 can include a clamp or other removable attachment device (e.g., vice, bracket, brace, adhesive, or the like) for removably positioning the reference marker on the portion of the patient's anatomy. The type of attachment device can depend on what portion of the patient's anatomy the reference marker 102 is positioned on and/or the type of surgical procedure. The image acquisition device(s) 106 can detect the reference marker 102 and can be for example, at least one camera, IR camera, a charge coupled device (CCD), a complementary metal oxide semiconductor (CMOS) device, a charge injection device (CID), or the like. The image acquisition device(s) 106 can also detect an area surrounding the reference marker that can include at least parts of the body (e.g., anatomy) of the patient undergoing the surgical procedure and one or more surgical tools used during the surgical procedure (e.g., a handheld tool or a tool held by or attached to an end effector of a stereotactic surgical robot). The image acquisition device(s) 106 may also detect the bump detection sensor(s) at one or more times during the surgical procedure.

The bump detection sensor(s) 104 can have a lower profile (e.g., can be physically smaller and/or shorter) than the reference marker 102 so that the bump detection sensor (s) are less likely to be jostled than the reference marker. The bump detection sensor(s) 104 can be one or more types of non-optically tracked position sensor and can therefore have a lower profile than the optically tracked reference marker 102. For example, the bump detection sensor(s) 104 can include one or more of an optical sensor, an accelerometer, a gyroscope, a magnetometer, a potentiometer, a Hall effect sensor, a linear variable displacement transducer, a strain gage, an ultrasonic sensor, an electromagnetic sensor, a laser distance measurement sensor, or the like. In some instances the bump detection sensor(s) 104 may be optically tracked position sensors, depending on the situation and the confidence in motion capture based sensors. In some instances, the bump detection sensor(s) 104 can also include a wireless transmitter, such as a radio frequency (RF) or Bluetooth™ chip and be in wireless and/or wired communication with the computing device 108. The bump detection sensor(s) 104 may include a power source and/or additional circuitry or elements for tracking position.

The computing device 108 can include at least the memory 110 (which can be non-transitory memory, as described above) and the processor 112. The memory 110 and/or the processor 112 can be embodied as hardware. The computing device 108 may also include a wireless transceiver, for wireless communication with one or more elements of the navigation system; a power source; a user interface; a display; communication ports, for wired communication with one or more elements of the navigation system; or the like. The computing device 108 can receive and/or store at least position information recorded by the bump detection sensor(s) 104 and the image acquisition device(s) 106. The computing device 108 can also receive and store data recorded at the initial image registration time from the CT or MR scan device. The memory 110 can store data including a static relationship between a position of the at least one bump detection senser 104 and a position of the reference marker 102 at the initial image registration time and a static relationship between the position of the reference marker and a position of the portion of the patient's anatomy at the initial image registration time. The memory 110 can store machine executable instructions, which are executable by the processor 112 to at least determine if the reference maker 102 is bumped, to determine if automatic re-registration is necessary, and to perform automatic re-registration (if deemed necessary).

Figure 2:
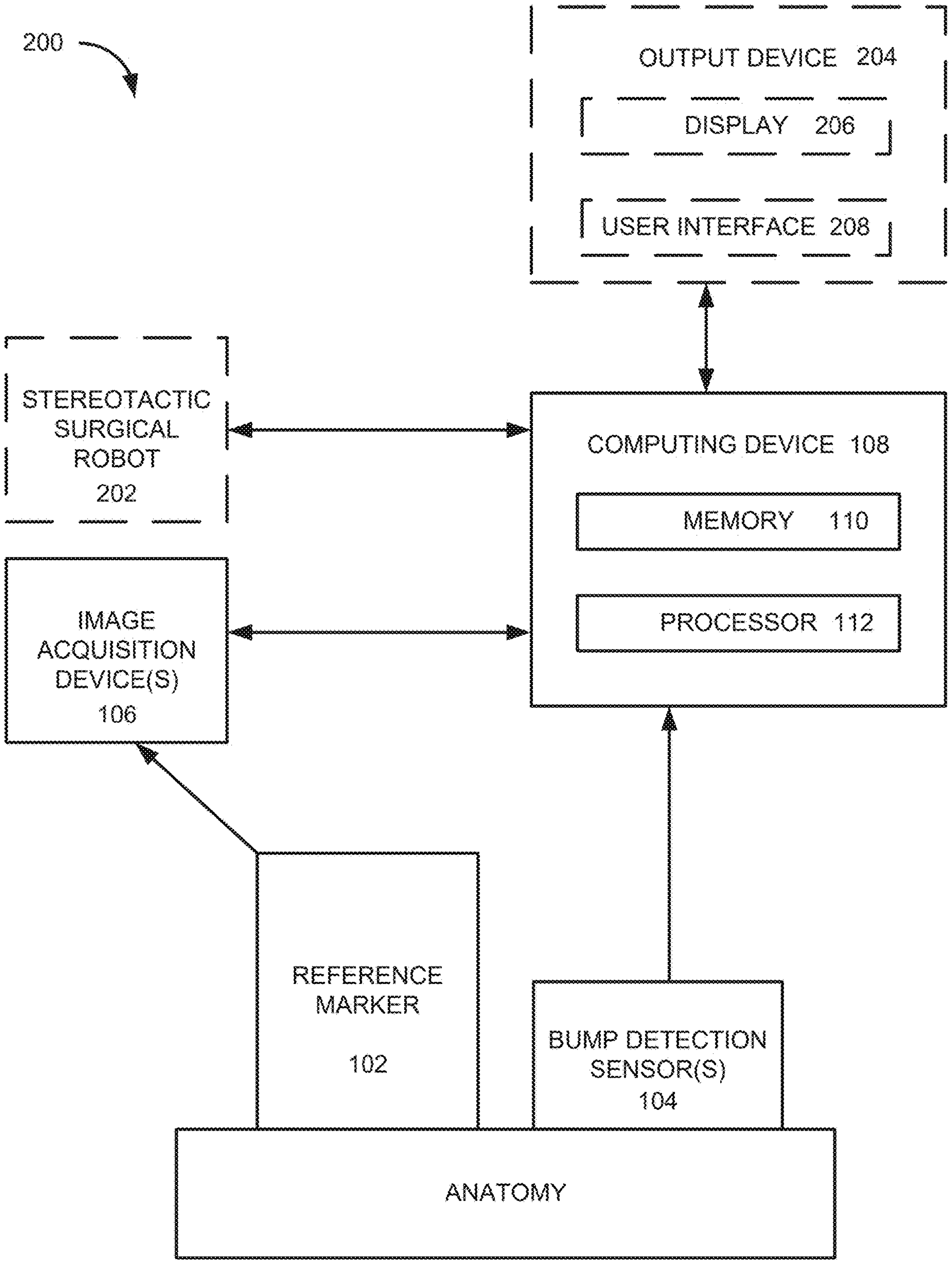
FIG. 2 is a diagram illustrating an example navigation system of FIG. 1.

FIG. 2 shows an example navigation system 200. It should be noted that each element of the navigation system 200 may have additional components that are not illustrated. The navigation system 200 includes all of the components of system 100 and shows the reference marker 102 and the bump detection sensor(s) 104 positioned on anatomy of a patient. System 200 can also include a stereotactic surgical robot 202 and/or an output device 204 for image guided surgery, which can either or both be in wired and/or wireless communication with the computing device 106 depending on the surgical procedure. The stereotactic surgical robot 202 can include at least an end effector (not shown) that can hold or be attached to one or more surgical implements for performing a surgical procedure. The computing device 108 can command the stereotactic surgical robot 202 and receive data (such as feedback information) from the stereotactic surgical robot. For example, the processor 112 can execute instructions to provide a trajectory to an end effector of the stereotactic surgical robot 202, relative to a given surgical procedure, based on at least positional information of the reference marker 102 and, in some instance, the bump detection sensor(s) 104. The processor 112 can then execute instructions to modify the trajectory provided to the stereotactic surgical robot 202 at least based on an automatic re-registration determined by the processor. The output device 204 may be used with the stereotactic surgical robot 202 or separately from the stereotactic surgical robot 202 with manual surgical tools (e.g., wielded by one or more members of the surgical team) for image guided surgery.

The output device 204 can include a display 206 and a user interface 208. The output device 204 can include other elements not shown such as an audio output, a power source, a wireless transceiver, or the like. The output device 204 can be a stand-alone device, such as a tv or computer monitor; a heads-up display; a virtual and/or augmented reality device; or the like. As mentioned above the output device 204 can be used for image guided surgery and can display, via display 206, at least one view of at least one portion of the patient's anatomy, the reference marker, and the at least one bump detection sensor. At least one surgical tool (not shown), manual and/or attached to the stereotactic surgical robot 202, may also be displayed by the display 206 of the output device 204. The at least one view can include the initial image registration view and/or a view at a given time during a surgical procedure. The at least one view can be augmented to show the at least one surgical tool and/or the path of the at least one surgical tool should take during a surgical procedure. In some instances, the navigation system 200 can include one or more surgical tools (that can be tracked by the system as additional bump detection sensor(s) 104) and the automatic re-registration can also be based on the proximity of the surgical tool to the reference marker 102 and the at least one bump detection sensor 104 positioned on the anatomy.

The output device 204 can additionally, and or alternatively, output one or more messages and/or warnings to the surgical team based on determinations performed by the computing device 108. The one or more messages and/or warnings can be output via visual, audible, and/or haptic means. The one or more messages and/or warnings can include, but are not limited to, asking for manual confirmation that the navigation system 200 should re-register the reference marker 102, alerting the surgical team that automatic re-registration will occur and/or has occurred, alerting the surgical team that a bump was detected, alerting the surgical team that the reference marker was bumped too severely for automatic re-registration to succeed, or the like. The output device 204 can also include a user interface 206 that can allow the surgical team to response to messages and/or warnings, to input positional or surgical information, and/or otherwise manually command the computing device 108 and all connected elements. For example, the user interface 208 of output device 204 can be used to input manual confirmation, when necessary, for the computing device 108 to perform automatic re-registration. The user interface 208 can include, but is not limited to, at least one of: a microphone, a mouse, a keyboard, a touch screen, a foot pedal, or the like.

Figure 3:
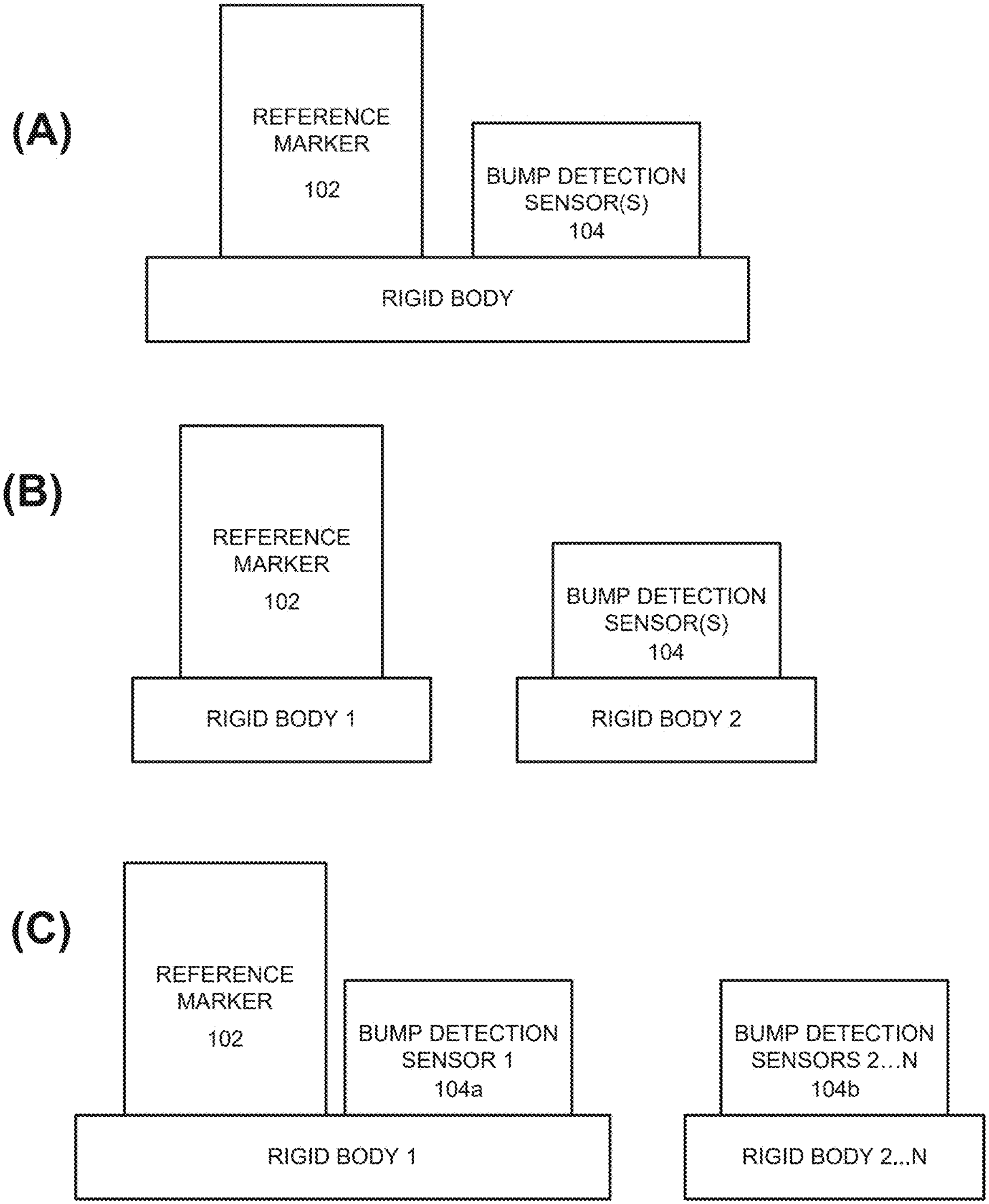
FIG. 3 is a diagram of example reference marker and bump detection sensor configurations for the system of FIG. 1.

Referring again to the reference marker 102 and the bump detection sensor(s) 104, FIG. 3 shows different non-limiting example configurations of positions for the reference marker and the bump detection sensor(s) in Elements A-C. While the reference marker 102 and the bump detection sensor(s) 104 are shown as sitting on top of rigid bodies it should be understood that they can be connected to the rigid bodies in any of the manners discussed above. Element A of FIG. 3 shows an example configuration where the reference marker 102 and at least one bump detection sensor 104 can be positioned adjacent to each other on one rigid body. The rigid body can be anatomy, for example, a spinous process as discussed further with regards to FIG. 4, or a significantly rigid body part such as a femur, radius, ulna, tibia, clavicle, or the like. Element B of FIG. 3 shows another example configuration where the reference marker 102 and the bump detection sensor(s) 104 can be positioned on different rigid bodies. The reference marker 102 can be position on rigid body 1, which can be the portion of the patient's anatomy, and the bump detection sensor(s) 104 can be positioned on rigid body 2. Rigid body 2 can be another portion of the anatomy of the patient, a surgical table the patient is located on, an end effector of a stereotactic surgical robot working on the patient, or a surgical tool being used on the patient.

Element C of FIG. 3 shows an example configuration where the reference marker 102 and a first bump detection sensor 104*a* (e.g., bump detection sensor 1) can be positioned adjacent each other on a first rigid body (rigid body 1) and at least a second bump detection sensor 104*b* (bump detection sensors 2 . . . N, where N is an integer greater than 2) can be positioned on at least a second rigid body (rigid body 2 . . . N) that is different from the first. For example, the reference marker 102 and the first bump detection sensor 104*a* can be positioned on a portion of the patient's anatomy above where the surgical procedure is performed that is intended to remain stationary. And the at least a second bump detection sensor 104*b* can be positioned on at least the second rigid body 2 . . . N, which can be, but is not limited to, at least one of: a surgical table the patient is located on, an end effector of a stereotactic surgical robot working on the patient, or another portion of the patient's anatomy. In such an instance the at least the second bump detection sensor 104*b* can also be used by the navigation system to detect robotic compliance and/or a robot positioning error in a stereotactic surgical robot associated with the navigation system.

Figure 4:
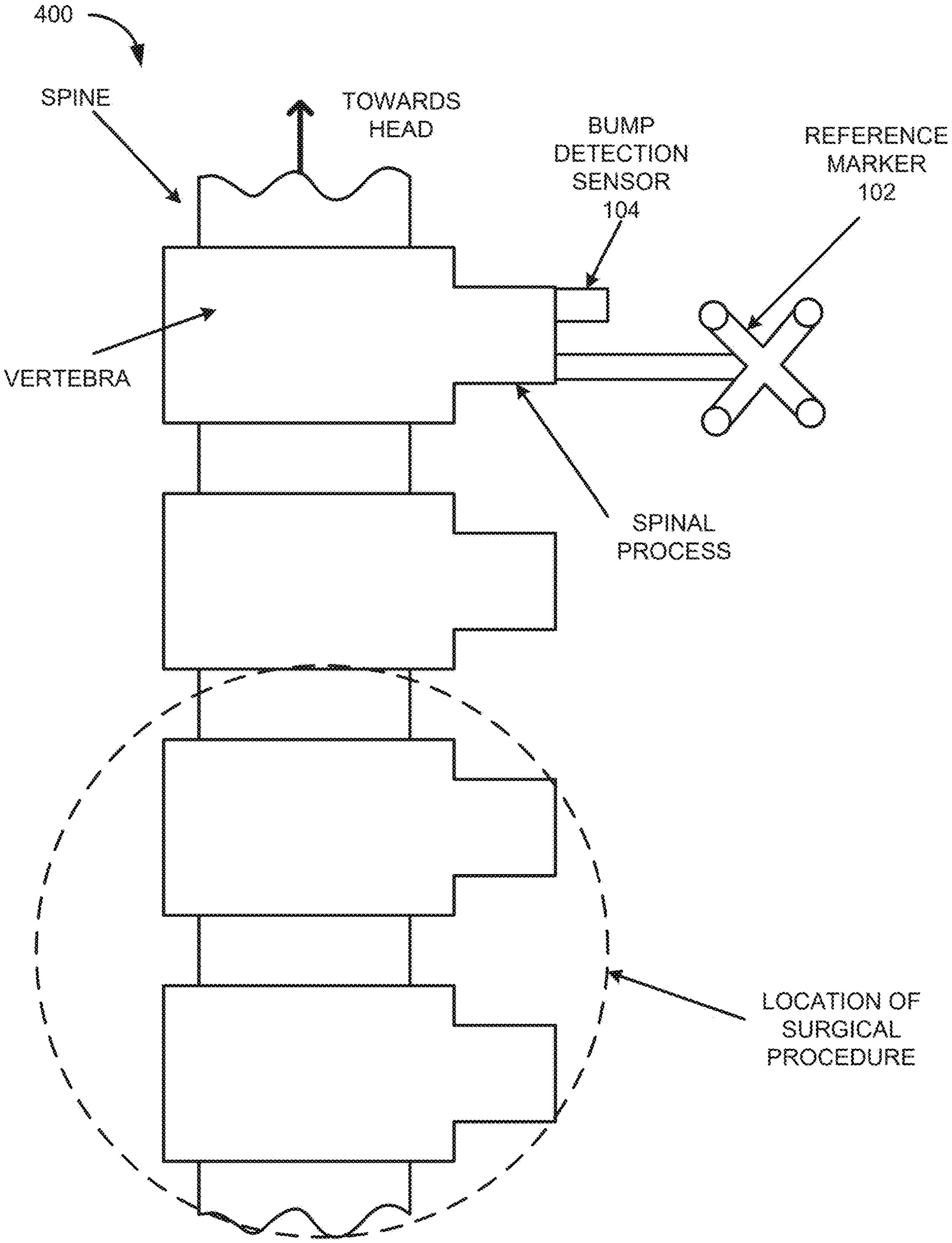
FIG. 4 is an illustration of a reference marker and bump detection sensor of FIG. 1 positioned for a surgical procedure on a spine.

FIG. 4 illustrates an example configuration 400 that can be used during a spinal surgical procedure. The example configuration 400 is similar to FIG. 3 element A, where a reference marker 102 and a bump detection sensor 104 are positioned adjacent each other on a portion of a patient's anatomy. Specifically, the reference marker 102 and the bump detection sensor 104 can be positioned on the same spinal process of a patient above an area of the spine being worked on during a spinal surgical procedure. The spinous processes above the area of work are traditionally considered rigid bodies for navigation based spinal surgical procedures. There is available bone remaining on the spinous process to attach to after the reference marker 102 is attached, and this can readily serve as a location to place the bump detection sensor 104. Because the bump detection sensor 105 can have a lower profile than the reference marker 102, because the bump detection sensor is not vision based, it can be positioned in more ways than a reference marker. It should be understood that FIG. 4 is a simplified illustration of a portion of the spine only to show an example positioning of the reference marker 102 and the bump detection sensor 104 and is not to scale. It should be similarly understood that the reference marker 102 and the bump detection sensor 104 can be any shape and/or size and are not limited to the illustrated example.

Figure 5:
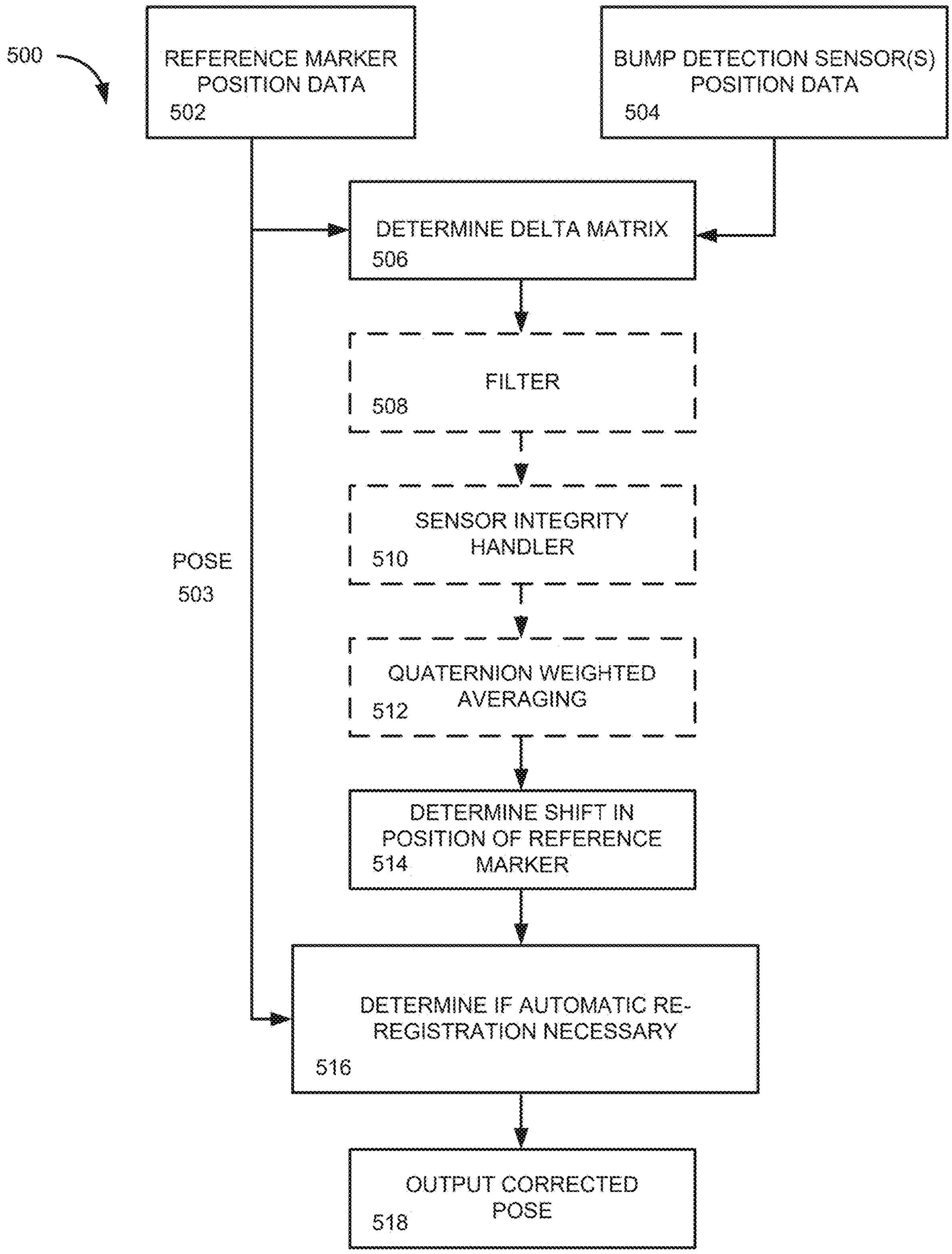
FIG. 5 is a diagram illustrating the control logic of bump detection and automatic re-registration that can be used by the system of FIG. 1.

Referring now to FIG. 5, which illustrates command instructions 500 the processor of the navigation system (e.g., processor 112 of computing device 108 of navigation systems 100/200) can execute. It should be understood that one or more commands can be performed in a different order than shown. At 502 the computing device can receive position data of an actual position of the reference marker at a time and at 504 the computing device can receive position data of an actual position of each of the at least one bump detection sensor at the time. At 506 the computing device can determine a delta matrix based on the position data of the actual position of the reference marker at the time, the position data of the actual position of each of the at least one bump detect sensor at the time, and the static relationship between the positions of the at least one bump detection senser and the reference marker at the initial image registration time, which was stored in memory. For example, using equation 1:

$$T_{PAct\_PDig} = T_{w1\_PAct}{}^{-1} T_{w1\_Ai} T_{Ai\_PDig} \quad \text{(EQ. 1)}$$

Where: $T_{PAct\_PDig}$ is the delta matrix; the delta matrix is the dynamic relationship between a location of the reference marker 102 (where the reference marker 102 reports that it is) (PAct) and the position of where the reference marker was relative to the bump detection sensor(s) when first registered (used as a measure of where the reference marker 102 was relative to the anatomy at registration) (PDig); $T_{w1\_PAct}$ is actual position of the reference marker 102 with respect to W1 (the common reference frame) at a given time; $T_{w1\_Ai}$ is the actual position of a bump detection sensor(s) 104 with respect to W1 (the common reference frame) at a given time; and $T_{Ai\_PDig}$ is the static relationship between bump detection sensor(s) 104 and reference marker at registration.

The calculation described above occurs when a single bump detection sensor(s) 104 is detected. If more than one bump detection sensor(s) 104 are detected, then the delta matrix can be an average for all of the bump detection sensors relative to the reference marker and, in some instances, weighted as discussed in the next paragraph.

At 508 the computing device can, optionally, filter at least the delta matrix. This step can low pass filters the delta matrix values to prevent discontinuities and minimize noise. The assumption made is that even though the bump detection sensor values may change rapidly from a quick move of the anatomy overall, the reference marker is also likely moving at a fast rate. Therefore, the delta matrix between the reference marker and the bump detection sensor(s) does not change at as high of a rate and since the filtering is only applied to the delta matrix, high frequency movements of the system will not necessarily be filtered out. Filtering can provide smooth and more accurate data or motion, for example if the navigation system includes a stereotactic robot. At 510 the computing device can, optionally run a sensor integrity handler to verify that the bump detection sensor(s) position values are reasonable. This can protect against the reporting of large delta values in the delta matrix, large rates of change of delta, and nonsense delta values in the delta matrix. For example, if a bump detection sensor stops working for any reason and there is no sensor value to use (typically reported as NaN), then the current reading should not be used in the pose correction process. If the bump detection sensor is found not to have values with integrity, then the computing device can re-use previous bump detection sensor delta matrix values that were valid at the previous time point. It is a 'last known good value' approach. If the sensor value is found to be valid in the future, then further filtering and/or interpolation can smooth any discontinuities between the current value and the last known good value. In general, the sensor integrity handler looks at both unfiltered, filtered, and averaged delta values in the delta matrix. At 512 quaternion weighted averaging can be applied to the delta matrix, which can be valid and filtered, of each of the bump detection sensors. Using quaternion mathematical operations that avoid singularities present in Euler angle based spatial relationships, the delta values of the delta matrices are all averaged based on the sensor weighting set by the user/system. Some bump detection sensors may be treated as more trustworthy and therefore may carry a higher weight in the averaging algorithm. A Kalman filter can also be used to dynamically set these weights. The resulting delta matrix from all the fused bump detection sensors can be applied the rest of the calculations if more than one bump detection sensor is utilized. Command instructions 508-512 are described in further detail (in another context) in U.S. Ser. No. 17/157,237, which is incorporated herein by reference in its entirety At 514 the computing device can determine the shift in the actual position of the reference marker relative to the position of the anatomy at the time based on the delta matrix and the static relationship between the positions of the reference marker and the portion of the patient's anatomy at the initial image registration time. The shift can be detected in any one of a variety of reference frames or coordinate systems but can be transformed to a common reference frame for calculations. For instance, the shift can be a shift in the reference marker relative to the registered position of the reference marker or the shift can be in another coordinate system such as a shift in where the bump detection sensor measures a portion of anatomy to be versus where the reference marker measures the portion of the anatomy to be. For example, the shift can be determined based on EQ. 2:

$$T_{PAct\_RB} = T_{PAct\_PDig} T_{PDig\_RB} \quad \text{(EQ. 2)}$$

Where: $T_{PAct\_RB}$=the relationship between the reference marker and the portion of the anatomy; and $T_{PDig\_RB}$=the static original position of the reference marker relative to the portion of the anatomy at an initial image registration.

At 516 the computing device can determine whether automatic re-registration is required based on one or more predefined thresholds. The shift in position of the reference marker can be compared to the one or more predefined thresholds based on the pose (position and orientation) information 503 of the reference marker at one or more times (e.g., the current time and/or the previous time). If automatic re-registration is determined to be necessary, then at 518 the computing device can, optionally, output a corrected pose of the reference marker. The corrected pose can then be applied to a trajectory of a stereotactic surgical robot and/or an image guidance software. For example, the corrected pose can be determined based on a calculated corrected relationship between the new, shifted position of the reference marker and the portion of the patient's anatomy based on EQ. 3:

$$T_{W1\_PDig} = T_{W1\_PAct} T_{PAct\_PDig} \quad \text{(EQ. 3)}$$

Where: $T_{W1\_PDig}$=the re-registered position of the reference marker with respect to W1 (the common reference frame).

Figure 6:
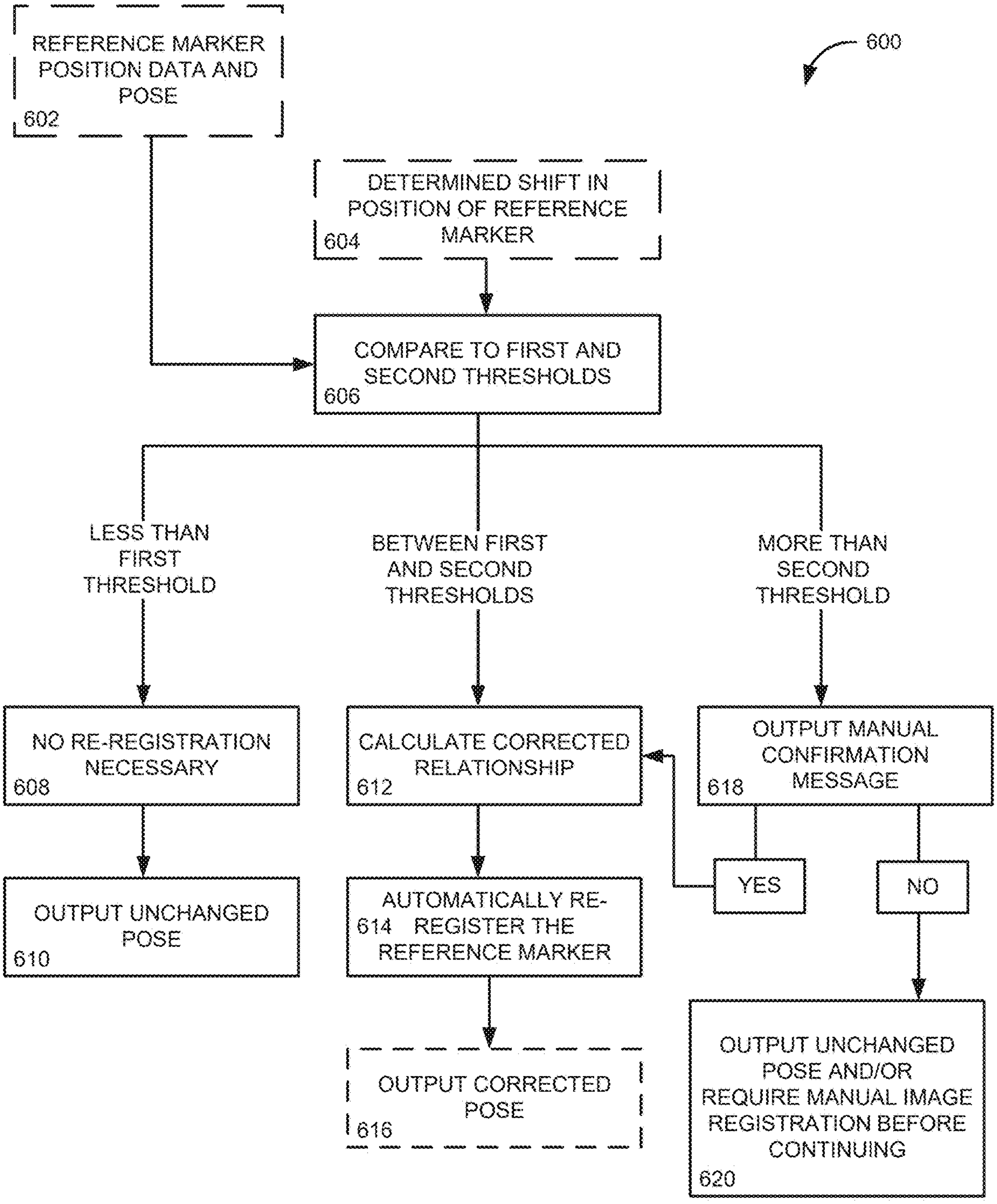
FIG. 6 is a diagram illustrating the control logic of determining if automatic re-registration is necessary from FIG. 5 that can be used by the system of FIG. 1.

FIG. 6 illustrates the command instructions 600 for the computing device to determine if an automatic re-registration is necessary at a time based on one or more predetermined thresholds. At 602 the computing device can receive the reference marker position data and pose and at 604 the determined shift in the position of the reference marker can be received into the automatic re-registration determination (e.g., 516 of FIG. 5) as previously described. At 606 the computing device can compare the determined shift in the position of the reference marker to a first and a second threshold of the one or more thresholds. The one or more thresholds can be predetermined by the surgical team and/or a maker of the navigation system based on the surgical procedure, patient information, and/or other tolerance limiting information. The shift can be detected in any one of a variety of reference frames or coordinate systems but can be transformed to a common reference frame for calculations. For instance, the shift can be a shift in the reference marker relative to the registered position of the reference marker or the shift can be in another coordinate system such as a shift in where the bump detection sensor measures a portion of anatomy to be versus where the reference marker measures the portion of the anatomy to be.

When the shift in the actual position of the reference marker relative to the position of the portion of the patient's anatomy at the time is less than a first predefined threshold, then at 608 the computing device can determine no re-registration is necessary and can output at 610 an unchanged pose. When the shift in the actual position of the reference marker relative to the position of the portion of the patient's anatomy at the time is between the first predefined threshold and a second predefined threshold, then the computing device can calculate at 612 a corrected relationship between a new, shifted position of the reference marker and the portion of the patient's anatomy, as described in more detail above. Then at 614 the computing device can automatically re-register the reference marker with the portion of the patient's anatomy and then at 616 output a corrected pose. The corrected pose can then be used to modify a trajectory and/or projection of a trajectory of a surgical tool, an end effector of a stereotactic robot, and/or modify a visualization of the surgical area.

At 618 when the shift in the actual position of the reference marker relative to the position of the portion of the patient's anatomy is greater than the second predefined threshold the computing device can output a message, via an output device (visual or audio, and optionally including a haptic alert), asking the surgical team if the navigation system should re-register the reference marker with the portion of the patient's anatomy. If the computing device receives confirmation, then the computing device can execute commands 612-616 as described above. If the computing device does not receive manual confirmation (e.g., the surgical team determined automatic re-registration was unnecessary and/or a full image registration was required, or the like), then the computing device can at 620 output an unchanged pose and/or require manual image registration before unlocking the navigation system to continue the surgical procedure, depending on the situation.

III. Methods

An aspect of the present disclosure can include methods 700-1100, shown in FIGS. 7-11 for detecting an unintended movement of a reference marker of a navigation system, determine whether a re-registration is necessary and, if needed, automatically re-registering the reference marker and changing an output of the navigation system. The methods can determine when a reference marker used during a surgical procedure experiences an unintended movement, referred to herein colloquially as a bump, from an initial registered position. The methods can also determine whether automatic re-registration is required after the bump is detected, and when needed, automatically re-register the reference marker and alter an output of the navigation system so the surgical procedure can proceed. The methods can thereby decrease the risk of injury to the patient, decrease the time a surgical procedure takes, and can decrease the amount of radiation exposure of the patient and the surgical team.

Figure 7:
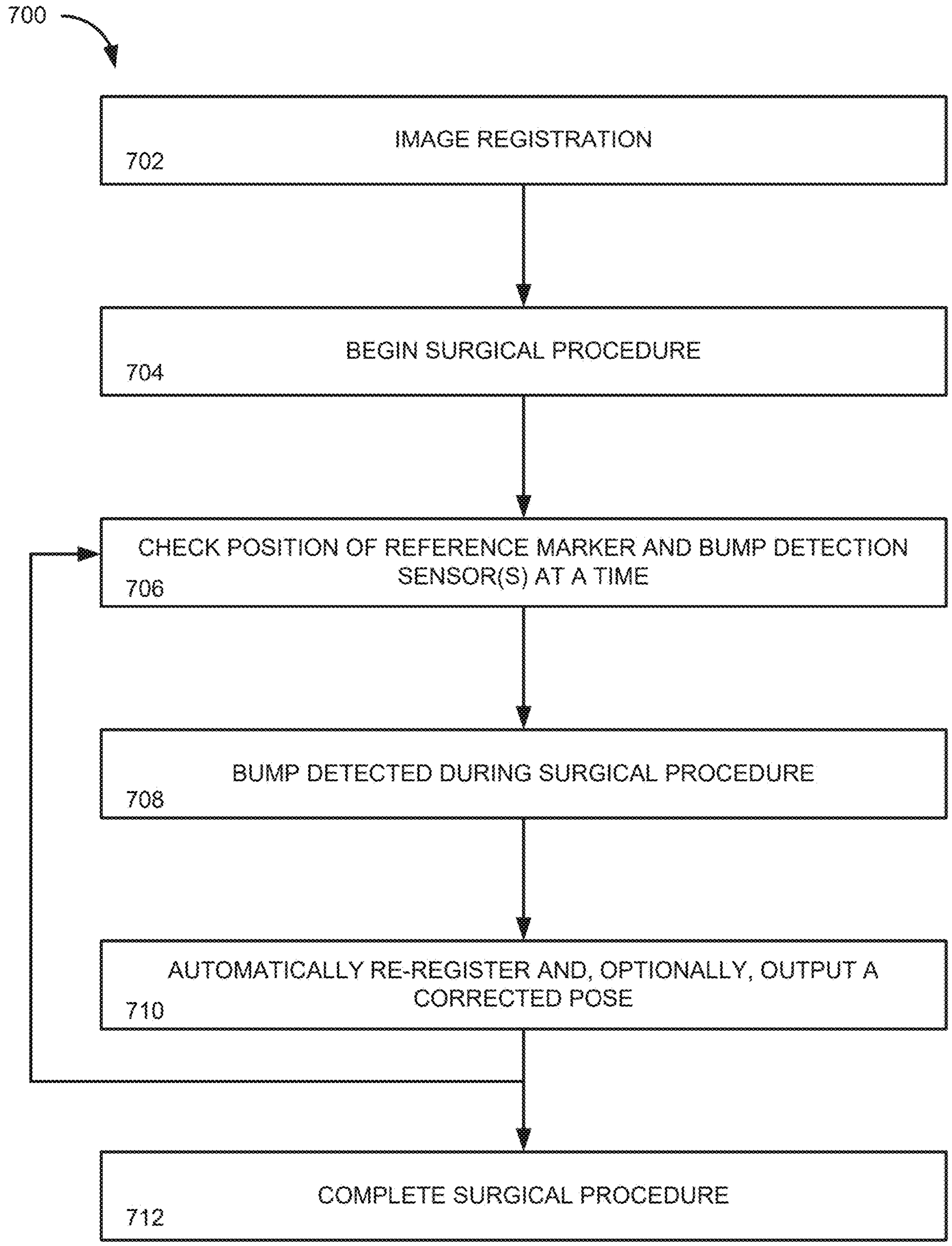
FIG. 7 is a process flow diagram illustrating methods for implementing the system of FIG. 1.

For purposes of simplicity, the methods 700-1100 are shown and described as being executed serially; however, it is to be understood and appreciated that the present disclosure is not limited by the illustrated order as some steps could occur in different orders and/or concurrently with other steps shown and described herein. Moreover, not all illustrated aspects may be required to implement the methods 700-1100, nor are methods 700-1100 limited to the illustrated aspects. Elements of methods 700-1100 can be performed by a computing device (including at least a memory and processor) of the navigation system Referring now to FIG. 7, illustrated is a method 700 for performing a surgical procedure while using the navigation system (e.g., navigation system 100 or 200). At 702, image registration is performed on the patient at an initial image registration time with a CT scan or MR scan. The image registration includes at least imaging the portions of the anatomy relevant to the surgical procedure, the positioned reference marker (e.g., reference marker 102) and the at least one bump detection sensor (e.g., bump detection sensor(s) 104). The reference marker and the at least one bump detection sensor can be positioned adjacent each other on the same portion of the anatomy. The portion of the anatomy can be a rigid body above the area of work of the surgical procedure. Positional information from the image registration can be stored on a computing device (e.g., computing device 108) of the navigation system. The reference marker can be any marker that can be attached at the portion of the anatomy based on the type of surgical procedure and visible by an imaging acquisition device (e.g., image acquisition device 108) during the use of the navigation system. The at least one bump detection sensor can be an optical sensor, an accelerometer, a gyroscope, a magnetometer, a potentiometer, a Hall effect sensor, a linear variable displacement transducer, a strain gage, an ultrasonic sensor, an electromagnetic sensor, and/or a laser distance measurement sensor. If more than one bump detection sensor is utilized then a first bump detections sensor can be positioned on the portion of the patient's anatomy and at least a second bump detection sensor positioned on at least one of: a surgical table the patient is located on, an end effector of a stereotactic surgical robot working on the patient, or another portion of the patient's anatomy.

At 704, the image guided or stereotactic surgical procedure can be commenced on the patient with the navigation system in use. At 706, the position of the reference marker and the bump detection sensors can be checked at a time. The positions can be checked at a predetermined rate or a rate chosen by a member of the surgical team (e.g., once every half a second, once a second, once every five seconds, once every thirty seconds, or the like) through part or all of the surgical procedure. If no bumps (shifts) to the reference marker's initial position relative to the portion of the anatomy the reference marker is positioned on are detected then, the surgical procedure continues as normal. However, if a bump (shift in the position) of the reference marker is detected, at 708, by the navigation system, then the navigation system can determine the amount of the shift of the reference marker from the reference marker's initial image registered position relative to the anatomy. The shift can be due to an unintended disruptive contact of the reference marker during, for example, spine surgery, neurosurgery, or orthopedic surgery.

At 710, the navigation system can automatically re-registers the new, shifted position of the reference marker and, optionally, output a corrected pose of the reference marker. To determine if the navigation system should automatically re-register the reference marker the shift of the reference marker from the reference marker's initial image registered position relative to the anatomy is compared to one or more predefined thresholds. The shift can be detected in any one of a variety of reference frames or coordinate systems but can be transformed to a common reference frame for calculations. For instance, the shift can be a shift in the reference marker relative to the registered position of the reference marker or the shift can be in another coordinate system such as a shift in where the bump detection sensor measures a portion of anatomy to be versus where the reference marker measures the portion of the anatomy to be. If the navigation system determines an automatic re-registration is needed, then the automatic re-registration can be performed and a corrected relationship and, optionally, the corrected pose can be fed into image guided surgery software and/or stereotactic surgical robot control software so the surgical procedure can proceed without significant interruption. The navigation system can run through steps 706-710 as many times as required during a surgical procedure. At 712, the surgical procedure can be completed, with optimized time management, less patient safety risk, and minimum radiation exposure.

Figure 8:
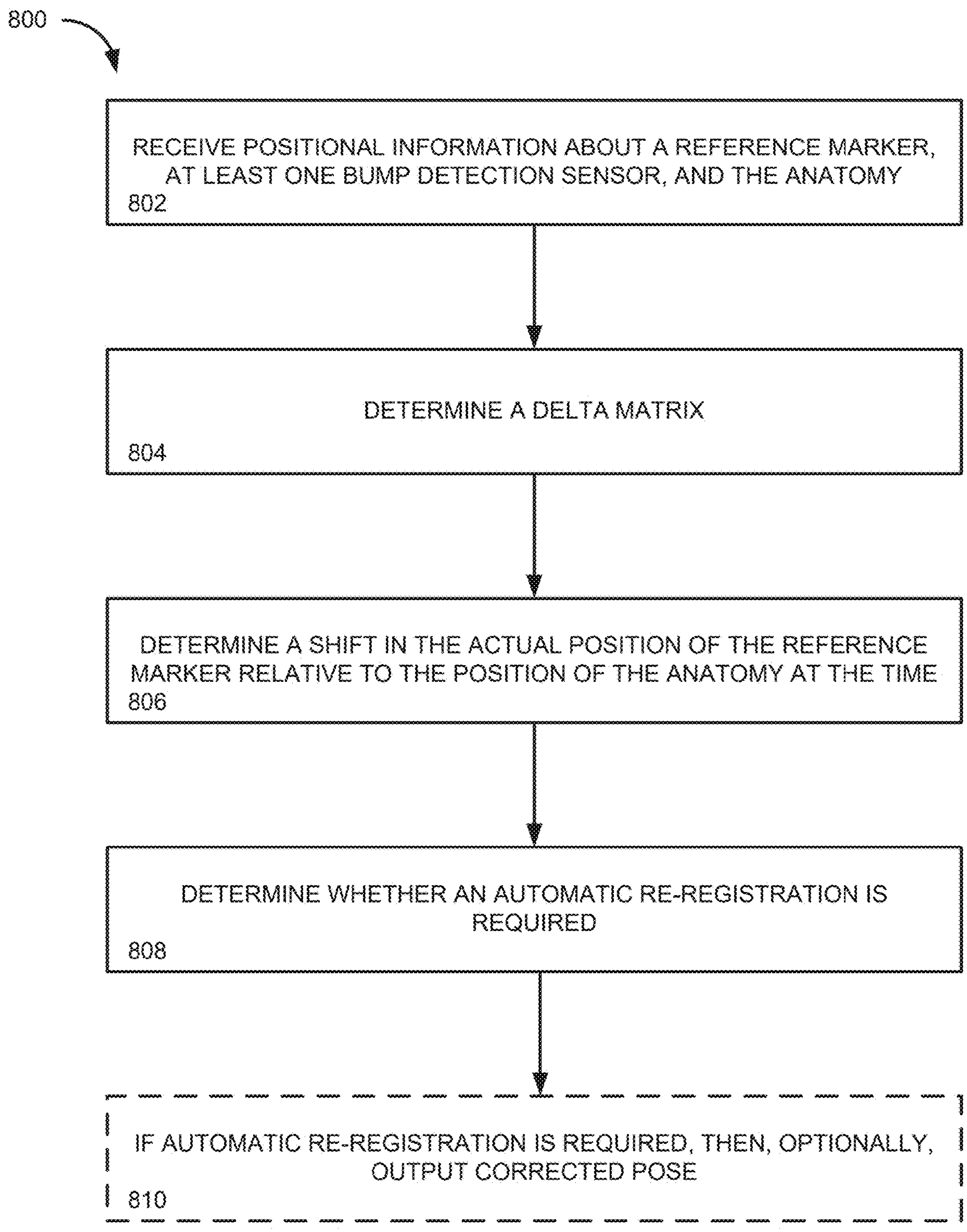
FIG. 8 is a process flow diagram illustrating methods for bump detection and automatic re-registration.

Referring now to FIG. 8, illustrated is a method 800 for use of the navigation system with enhanced reference marker placement to improve a surgical procedure for a patient. The method 800 can improve/enhance patient treatment during a surgical procedure by ensuring that a reference marker position is well tracked for improved safety and effectiveness. For example, the method 800 can be used during a spine surgery. At 802, positional information can be received by a computing device (e.g., computing device 108 including memory 110 and processor 112). The positional information can be information about a reference marker detectable by an image acquisition device and positioned on a portion of a patient's anatomy and at least one bump detection sensor, which can have a lower profile than the reference marker. The reference marker, the at least one bump detection sensor, and the portion of the patient's anatomy can be image registered at an initial image registration time, such as described with respect to method 700. The positional information can include: a static relationship between a position of the at least one bump detection senser and a position of the reference marker at the initial image registration time, a static relationship between the position of the reference marker and a position of the portion of the patient's anatomy at the initial image registration time. position data of an actual position of the reference marker at a time, and position data of an actual position of each of the at least one bump detection sensor at the time. If the method is used during a spine surgery, then the reference marker can be positioned on a spinal process of the patient above an area of the spine undergoing the spine surgery and the at least one bump detection sensor can be positioned on the same spinal process of the patient.

At 804, a delta matrix can be determined by the computing device based on the position data of the actual position of the reference marker at the time, the position data of the actual position of each of the at least one bump detect sensor at the time, and the static relationship between the positions of the at least one bump detection senser and the reference marker at the initial image registration time. For one or more bump detection sensors, the delta matrix can be calculated as described above with respect to FIG. 5 and the associated description. At 806, the shift in the actual position of the reference marker relative to the position of the anatomy at the time can be determined by the computing device based on the delta matrix and the static relationship between the positions of the reference marker and the portion of the patient's anatomy at the initial image registration time. The shift in the actual position of the reference marker can also be calculated as described above with respect to FIG. 5 and the associated description. At 808, a determination can be made by the computing device as to whether automatic re-registration is required based on one or more predefined thresholds. The determination is described in more detail with respect to FIG. 9 and method 900. At 810, if the computing device determined automatic re-registration is required, then the computing device can perform the automatic re-registration, as described in detail above, and, optionally, output the corrected pose based on the automatic re-registration for use with an image guided surgery software and/or a stereotactic surgical robot.

Figure 9:
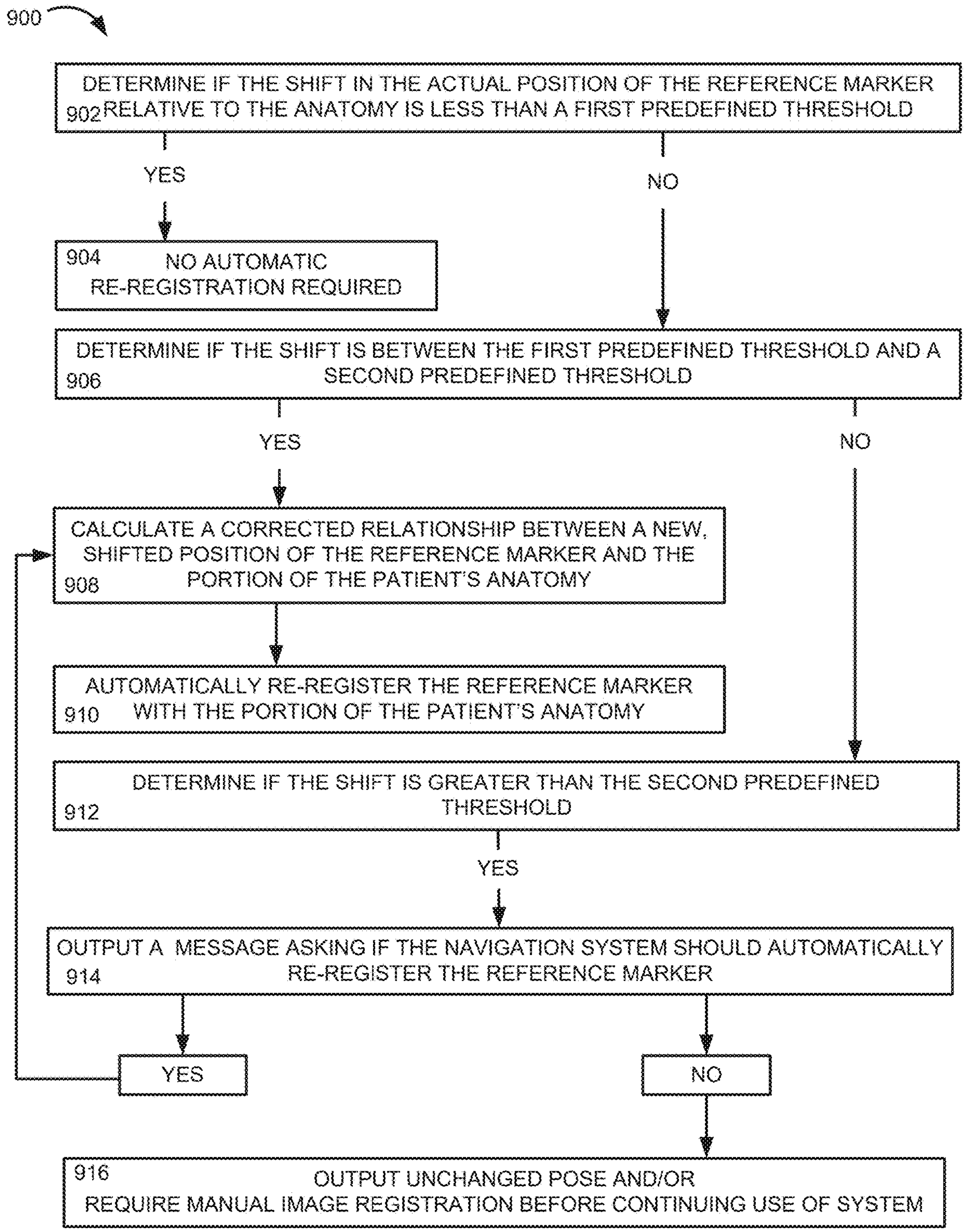
FIG. 9 is a process flow diagram illustrating methods for determining if automatic re-registration is required.

Referring now to FIG. 9, illustrated is a method 900 for a navigation system to determine if an automatic re-registration is required based on the one or more predefined thresholds and to automatically re-register the new, shifted position of the reference marker with the portion of the anatomy. At 902, a determination can be made by the computing device on whether the shift in the actual position of the reference marker relative to the portion of the anatomy is less than a first predefined threshold. If the shift in the actual position of the reference marker relative to the position of the portion of the patient's anatomy at the time is less than the first predefined threshold, then, at 904, the computing device can determine that no automatic re-registration is required. If no-automatic re-registration is required at the time, then the system can continue to check at the next time.

If the shift in the actual position of the reference marker relative to the portion of the anatomy is greater than the first predefined threshold, then, at 906, a determination can be made by the computing device whether the shift in the position of the reference marker is between the first predefined threshold and a second predefined threshold. If the shift in the actual position of the reference marker relative to the position of the portion of the patient's anatomy at the time is determined to be between the first predefined threshold and the second predefined threshold, then the computing device can determine that automatic re-registration is required. If automatic re-registration is required, then, at 908, the computing device can calculate a corrected relationship between a new, shifted position of the reference marker and the portion of the patient's anatomy. At 910, the computing device can use the corrected relationship to automatically re-register the new shifted position of the reference marker with the portion of the patient's anatomy. The automatically re-registered position of the reference marker can be used, optionally, to output a corrected to pose to the image guided surgery software and/or the stereotactic surgical robot to alter an image, a projection and/or a trajectory.

At 912, a determination can be made by the computing device that the shift in the actual position of the reference marker relative to the portion of the anatomy is greater than the second predefined threshold (as it is not less than the first predefined threshold or between the first predefined threshold and the second predefined threshold). It should be noted that while shown and described as sequential the threshold comparisons can be simultaneous. When the shift in the actual position of the reference marker relative to the portion of the anatomy is greater than the second predefined threshold, then manual confirmation is required before automatic re-registration can take place. At 914, a message can by output by the computing device (e.g., via an output device associated with the computing device) asking if the navigation system should automatically re-register the reference marker. If the computing device receives confirmation, then the computing device can calculate at 908, the corrected relationship between the new, shifted position of the reference marker and the portion of the patient's anatomy, and, at 910, re-register the new, shifted position of the reference marker with the portion of the patient's anatomy. Confirmation can be received by the computing device via a user interface associated with the computing device. If no manual confirmation is received, then at 916, the computing device can output an unchanged pose and/or require manual image registration before continuing use of the system, depending on the situation.

Referring now to FIG. 10, illustrated is a method 1000 for implementing the navigation system with a stereotactic surgical robot for a surgical procedure. At 1002, a trajectory can be provided by a computing device to an end effector of a stereotactic surgical robot associated with the computing device relative to a given surgical procedure (e.g., neurosurgery, tumor ablation, or the like). The surgical procedure with the stereotactic surgical robot can proceed as normal with the navigation system acting to check for unwanted changes in the position of the reference marker at a predetermined rate.

Optionally, at 1004, the computing device can also detect for compliance and/or position error in the stereotactic surgical robot if the at least one bump detection sensor is at least two. For example, if more than one bump detection sensor is utilized then a first bump detections sensor can be positioned on the portion of the patient's anatomy and at least a second bump detection sensor positioned on at least one of: a surgical table the patient is located on, an end effector of a stereotactic surgical robot working on the patient, or another portion of the patient's anatomy. The computing device can utilize the positional information from the at least the second bump detection sensor, which can be positioned on the robot, to detect for compliance and/or position error in the robot. If an unwanted change in the position (e.g., a bump) of the reference marker is determined and/or compliance and/or position error in the robot is detected, then, at 1006, the computing device can determine whether an automatic re-registration of the reference marker is necessary to keep the trajectory accurate and precise based on the one or more predefined thresholds. The determination can be as described above.

At 1008, if automatic re-registration is determined to be required, then the computing device can automatically re-register the reference marker with the anatomy and can, optionally, output a corrected pose. The computing device can calculate a corrected relationship between the new, shifted position of the reference marker and the portion of the patient's anatomy. The computing device can use the corrected relationship to automatically re-register the new shifted position of the reference marker with the portion of the patient's anatomy. The automatically re-registered position of the reference marker may be used to output the corrected pose. At 1010, the trajectory of the end effector can be modified by the computing device in response to the re-registration and, optionally, the corrected pose output by the automatic re-registration. At 1012, the modified trajectory can be output to the end effector of the stereotactic surgical robot so the surgical procedure can be continued with optimized time management, less patient safety risk, and minimum radiation exposure.

Figure 11:
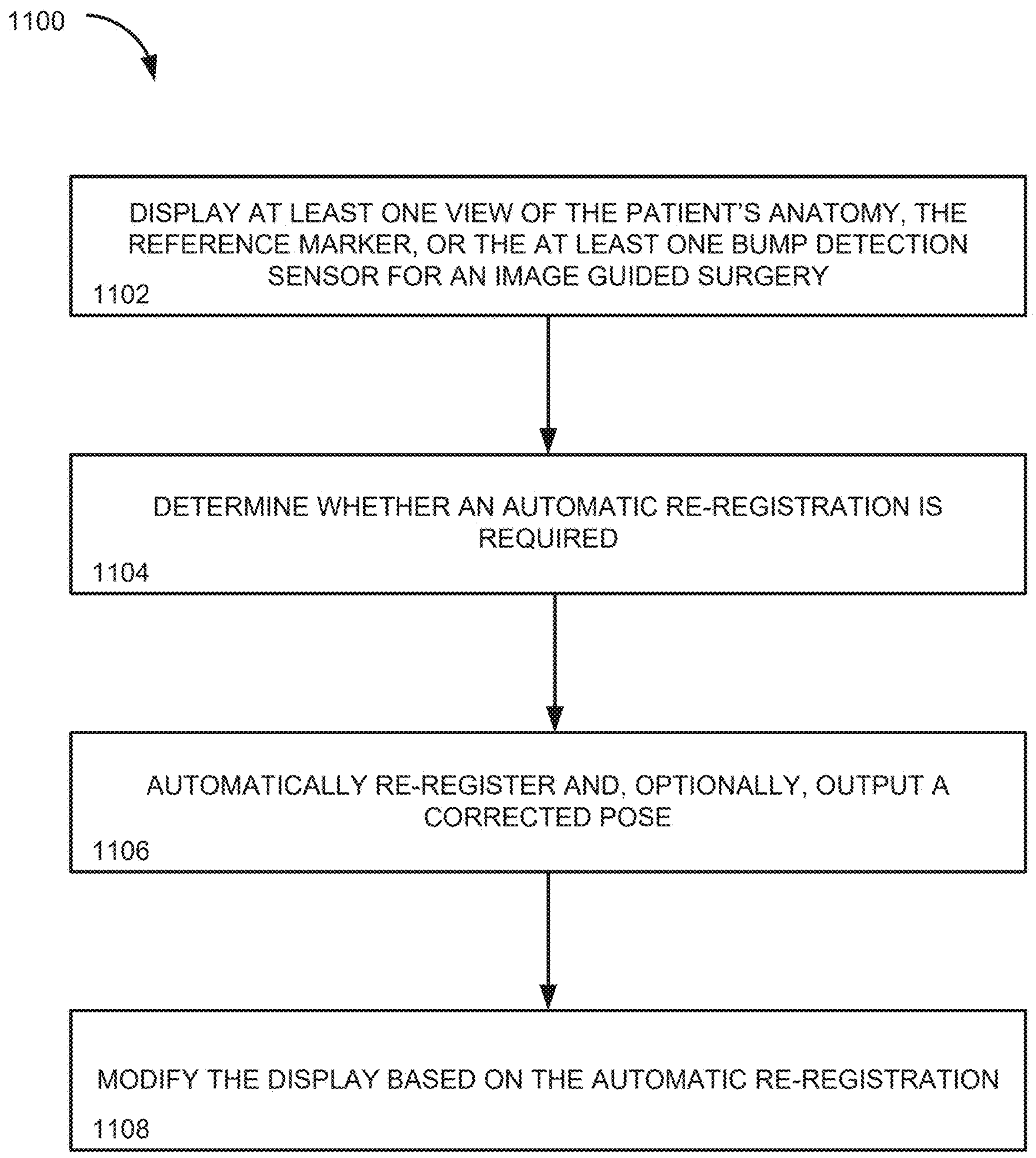
FIG. 11 is a process flow diagram illustrating methods for bump detection and automatic re-registration for implementation with an image guided surgical system.

Referring now to FIG. 11, illustrated is a method 1100 for implementing the navigation system with image guiding surgery and an output device including a display. At 1102, at least one view of at least one of the portion of the patient's anatomy, the reference marker, or the at least one bump detection sensor can be displayed by the computing device on the display of the output device associated with the computing device. The display can also include a view of one or more surgical tools and/or projections of where the one or more surgical tools should be based on the surgical procedure and the type of image guided surgery. The output device can be, for example, a computer or TV monitor, a heads-up display, an AR/VR headset, or the like. The image guided surgical procedure can proceed as normal with the navigation system acting to check for unwanted changes in the position of the reference marker at a predetermined rate. If an unwanted change in the position (e.g., a bump) of the reference marker is determined then, at 1104, the computing device can determine whether an automatic re-registration of the reference marker is required to keep the display accurate and precise based on the one or more predefined thresholds. The determination can be as described above.

At 1106, if automatic re-registration is determined to be required then the computing device can perform the automatic re-registration and, optionally, output a corrected pose. The computing device can calculate a corrected relationship between the new, shifted position of the reference marker and the portion of the patient's anatomy. The computing device can use the corrected relationship to automatically re-register the new shifted position of the reference marker with the portion of the patient's anatomy. The automatically re-registered position of the reference marker may be used to output the corrected to pose. At 1108, the display can be modified by the computing device in response to the automatic re-registration. The modification can be to one or more views of the anatomy, reference marker, and/or bump detection sensor(s). The modification can also be to a view of the one or more surgical tool or the projection of where the surgical tool should move to next. The modifications to the display can allow the surgical team to continue the surgical procedure with optimized time management, less patient safety risk, and minimum radiation exposure.

IV. Example Case Study

The following example case study demonstrates a use of the systems and methods described above with respect to an intraoperative navigation of a spinal surgery.

Figure 12:
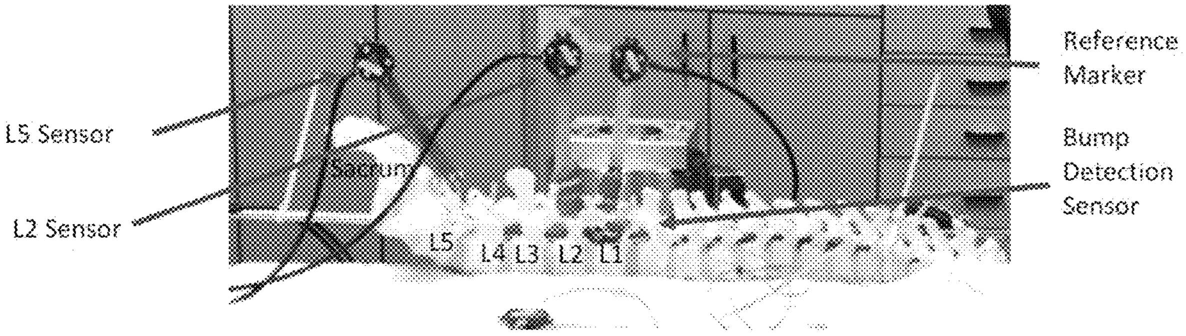
FIG. 12 is an experimental set up to for testing the system of FIG. 1.

The case study was completed utilizing a sawbones spine with rigid body markers on the spinous processes of L1, L2, and L5, as well as an additional sensor on the transverse process of L1 (see FIG. 12). The rigid body markers were Optotrak Certus position markers (referred to as optotrak markers), seen in FIG. 12 as disks with small circles. The Optotrak Certus is a motion capture system that offers flexibility for motion capture applications through its accuracy of up to 0.1 mm, resolution of 0.01 mm, maximum high-speed marker frequency of 4600 Hz, portable design, and position markers that include inline wiring and branching technology that provide freedom of movement. The Optotrak system is similar to clinically used surgical navigation systems in that it is an optical based tracking system utilizing a stereoscopic camera. The sensor on the spinous process of L1 was designated the reference marker to which the positions of L2 and L5 were considered relatively positioned to for the purposes of the study. The sensor on the transverse process of L1 was designated as the bump detection sensor (referred to as the bump detection and correction sensor). All optotrak markers with visual tracking were utilized for ease of testing, however it is to be understood that any of the sensor types described above can easily replace the optical tracking sensor on the transverse process of L1.

After mounting the optotrak markers, the L2 and L5 vertebra were digitized. Digitization was the equivalent of registering the spine anatomy to the reference marker via a CT scan, which is the current clinical standard. After digitization, the location of L2 and L5 were given by the markers mounted directly to L2 and L5. Because these sensors were mounted directly to the respective vertebra, these sensors were considered 100% accurate representations of where the L2 and L5 vertebra were throughout testing. The reference marker and the bump detection and correction sensor (both optotrak markers) on L1 also output the location of L2 and L5. The locations determined by the reference marker and the bump detection and correction sensor were compared with the accurate representations from the sensors on L2 and L5.

Tests were repeated four times and were each roughly one minute in length. The tests consisted of the following steps. (1) Acquiring baseline spatial relationships between the reference marker on L1, the bump detection and correction sensor on L1, the sensor on L2, and the sensor on L5. Stationary reading from the sensors occurred from 0 to 7 second in FIGS. 13-15. (2) Turning off the auto registration by occluding the bump detection and correction sensor on L1 from 7 seconds to 26 seconds. (3) Simulating bumping the reference sensor in a surgical setting with only existing image-based registration technology. The reference marker on L1 was rotated with respect to the spine between 7 and 26 seconds while the bump detection and correction sensor on L1 was occluded. (4) Turning on the auto registration by uncovering the bump detection sensor at second 26. (5) Acquiring new spatial relationships between the reference marker on L1, the bump detection and correction sensor on L1, the sensor on L2, and the sensor on L5 by getting stationary readings from 26 seconds to 33 seconds. (6) Simulating bumping the reference marker in a surgical setting with the new invention. The reference marker on L1 was rotated with respect to the spine between 33 seconds and 42 second while the bump detection and correction sensor on L1 is fully visible. (7) Demonstrating auto reregistration with the algorithm enabled by acquiring stationary readings from the reference marker on L1, the bump detection and correction sensor on L1, the sensor on L2, and the sensor on L5 from second 42 to the end of the test.

Figure 13:
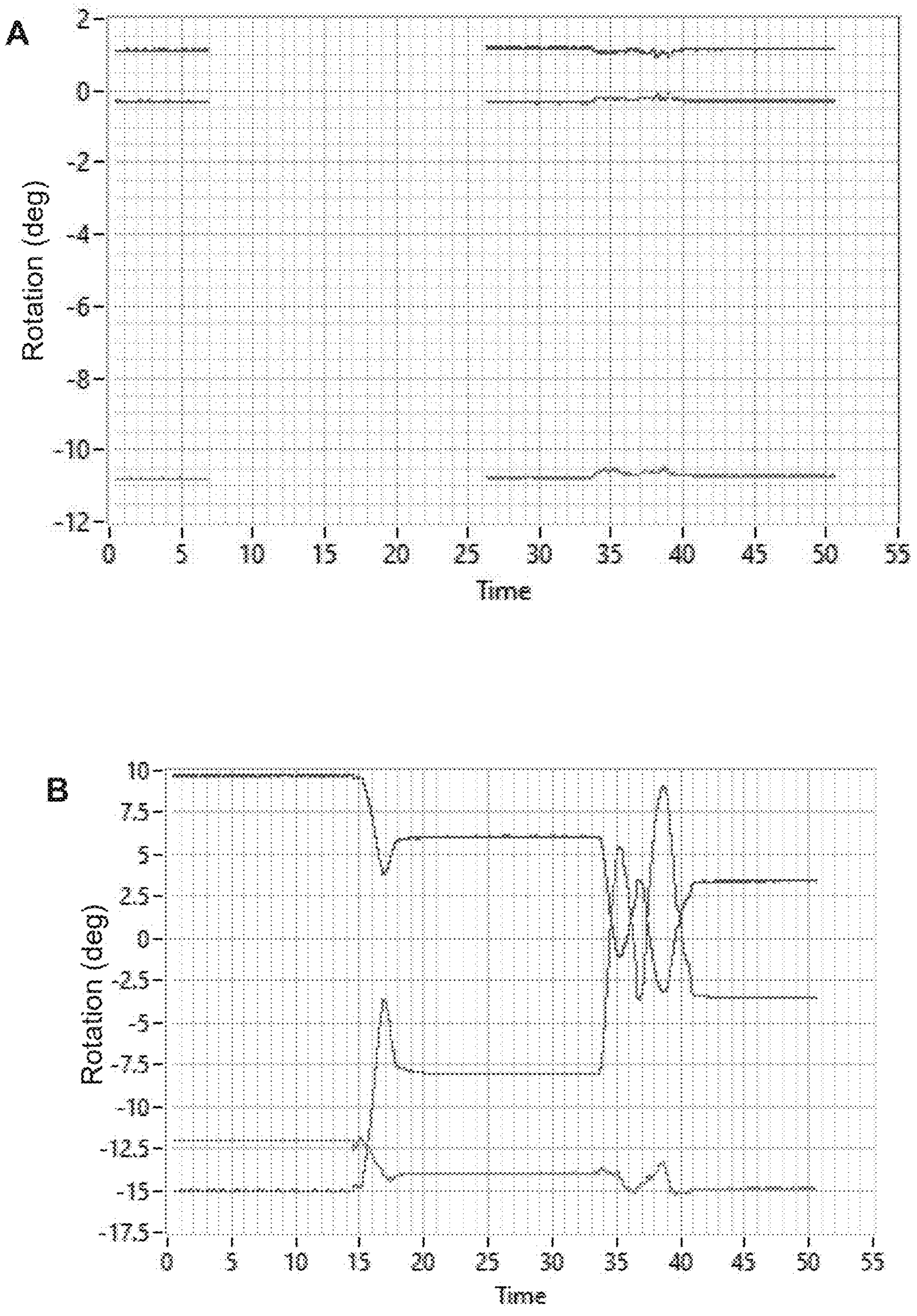
FIGS. 13-15 are graphical representations of experimental data.

FIG. 13, left plot (element A), shows that from roughly 7 seconds to 26 seconds the bump detection and correction sensor was occluded, which effectively disabled the auto registration. During this same time (7-26 seconds) the reference marker was rotated, as shown in FIG. 13, right plot (element B), which was representative of the reference marker being bumped. Again, at seconds 33 to 42 the reference marker was rotated. During this time the bump detection and correction sensor was made visible (thereby turning on auto reregistration). Note that this was not a completely rigid setup and there was some small movement of the bump detection and correction sensor due to the rotation of the reference array causing the L1 vertebra to move slightly.

The initial registration of the sawbones (e.g., the anatomy) to the sensors was used to compute motion of the sawbones (e.g., the anatomy) in clinically relevant reference frames. This is the equivalent to the surgical navigation system providing the spatial relationships given the CT data and the reference marker position. Registration errors caused by the bumped reference sensor are shown as errors in FIGS. 14 and 15. These values show clearly why bumping a reference marker can have devastating consequences if not detected by the surgical team. The error between where the L2 sensor (ground truth) and the L1 sensors (reference marker and bump detection and correction sensor) thought L2 was plotted below (shown in FIG. 14).

Figure 14:
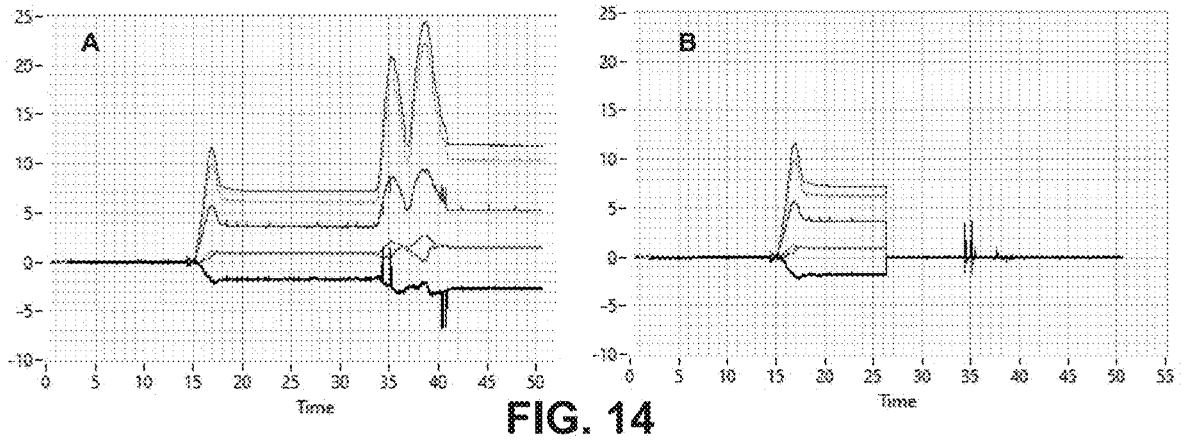

FIG. 14 shows 3 lines that are translation of the L2 vertebra in mm and 3 lines that are rotation of the L2 vertebra in degrees. The left plot of FIG. 14 (element A) shows surgical registration error with existing registration technology. Specifically, it is the error between where the L2 sensor says the L2 vertebra is versus where the L1 reference marker says L2 is. The right plot of FIG. 14 (element B) shows surgical registration error with the new invention (except when disabled at 7-26 seconds). Specifically, it is the error between where the L2 sensor says the vertebra is versus where the fused output of the L1 reference marker and the L1 bump detection and correction sensor say L2 is.

Figure 15:
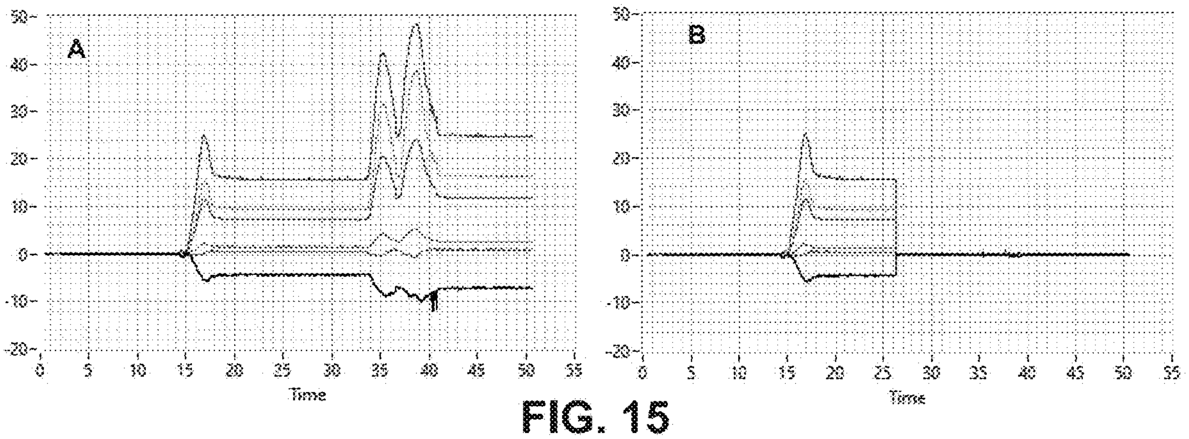

FIG. 15 shows 3 lines that are translation of the L5 vertebra in mm and 3 lines that are rotation of the L5 vertebra in degrees. The left plot of FIG. 15 (element A) shows surgical registration error with existing registration technology. Specifically, it is the error between where the L5 sensor says the L5 vertebra is versus where the L1 reference sensor says L5 is. The right plot of FIG. 15 (element B) shows surgical registration error with the new invention (except when disabled at 7-26 seconds). Specifically, it is the error between where the L5 sensor says the vertebra is vs where the fused output of the L1 reference sensor and the L1 bump detection and correction sensor say L5 is.

Comparing the left and right plots of FIGS. 14 and 15, one take away is that error is 0 in the right plots after time 26, when the bump detection and correction sensor is uncovered and made visible to the camera again. Prior to second 26 the left and right plots are virtually identical because either the reference marker has not been bumped (time 0-7) or the bump detection and correction sensor was not visible (time 7-26). Practically speaking, an error of 0 means that the system knows where the spine anatomy is with great accuracy and spine surgery complications due to bad navigation may be reduced. Current surgical navigation systems are best represented by the left plots of FIGS. 14 and 15: if the reference marker is inadvertently bumped an error is introduced and there is no second sensor to compensate. Note that the magnitude of the error is larger with L5 (shown in FIG. 15) compared to L2 (shown in FIG. 14) due to the further distance L5 is from the reference marker. This phenomenon also is a challenge in surgical navigation. This invention has the goal of augmenting surgical navigation systems to significantly reduce registration errors, as represented by the right plots of FIGS. 14 and 15.

In this experiment, the algorithm has suitably shown the ability of sensor fusion technology, an example of this technology is described in U.S. Ser. No. 17/157,237, which is incorporated herein by reference in its entirety, to compensate for reference marker movement and display correct positions of multiple levels of the spine. However, intraoperatively a visual-based technology cannot be utilized for the bump detection sensor due to line-of-sight concerns. Therefore, the same algorithm can be implemented with a different position tracking modality for the bump detection and correction sensor, such as a gyroscopic- and/or accelerometer-based tracking. From the algorithm's perspective the modality does not matter, it just needs reliable position data as an input. The Optotrak system was used for convenience for the case study as it was already in the lab and integrated with necessary software.

From the above description, those skilled in the art will perceive improvements, changes, and modifications. Such improvements, changes and modifications are within the skill of one in the art and are intended to be covered by the appended claims.

What is claimed is:

1. A method comprising: retrieving, by a computing device comprising a processor, data comprising a static relationship between a position of at least one bump detection sensor and a position of a reference marker at an initial image registration time and a static relationship between the position of the reference marker and a position of a portion of a patient's anatomy at the initial image registration time, wherein the reference marker is detectable by an image acquisition device and positioned on the portion of the patient's anatomy, wherein the reference marker, the at least one bump detection sensor, and the portion of the patient's anatomy are image registered together at the initial image registration time; receiving, by the computing device, position data of an actual position of the reference marker at a time as a procedure is being performed on the patient and position data of an actual position of each of the at least one bump detection sensor at the time as the procedure is being performed on the patient; determining, by the computing device, a delta matrix based on the position data of the actual position of the reference marker at the time, the position data of the actual position of each of the at least one bump detect sensor at the time, and the static relationship between the positions of the at least one bump detection sensor and the reference marker at the initial image registration time, wherein the delta matrix represents the dynamic relationship between the actual position of the reference marker at the time as the procedure is being performed on the patient and the static position of the reference marker relative to the at least one bump detection sensor at the initial registration time; calculating, by the computing device, a quantitative measure of a shift in the actual position of the reference marker relative to the position of the anatomy at the time the procedure is being performed on the patient by multiplying the delta matrix and the static relationship between the positions of the reference marker and the portion of the patient's anatomy at the initial image registration time; deciding, by the computing device, whether automatic re-registration is required by determining if the quantitative measure of the shift in the actual position of the reference marker relative to the position of the anatomy at the time as the procedure is being performed on the patient exceeds one or more predefined thresholds; based on at least one of the one or more predefined thresholds are exceeded and the automatic re-registration is required: performing, by the computing device, the automatic re-registration to update the static relationship between the position of the reference marker and the position of the portion of the patient's anatomy at the initial image registration time with a corrected relationship between the actual position of the reference marker and the portion of the patient anatomy at the time, and outputting, to a surgical assistive device, a corrected pose as the procedure is being performed on the patient based on the automatic re-registration.

2. The method of claim 1, based on at least one of the one or more predefined thresholds are exceeded and the automatic re-registration is required, the method further comprises: calculating, by the computing device, the corrected relationship between the actual position of the reference marker and the portion of the patient's anatomy at the time; and re-registering, by the computing device, the reference marker at the actual position with the portion of the patient's anatomy.

3. The method of claim 1, wherein the deciding whether the automatic re-registration is required further comprises: deciding, by the computing device, that no automatic re-registration is required based on the quantitative measure of the shift in the actual position of the reference marker relative to the position of the portion of the patient's anatomy at the time as the procedure is being performed on the patient is less than a first predefined threshold; deciding, by the computing device, that the automatic re-registration is required based on the quantitative measure of the shift in the actual position of the reference marker relative to the position of the portion of the patient's anatomy at the time exceeds the first predefined threshold and is less than a second predefined threshold; or deciding, by the computing device, that the automatic re-registration is required with manual confirmation before the automatic re-registration based on the quantitative measure of the shift in the actual position of the reference marker relative to the position of the portion of the patient's anatomy at the time is greater than a second predefined threshold.

4. The method of claim 3, wherein based on the automatic re-registration with manual confirmation is required, then the method further comprises: outputting, by the computing device via an output device, a message asking if the computing device should re-register the reference marker with the portion of the patient's anatomy; receiving, by the computing device via a user interface, a confirmation or a denial from a user; and upon receiving confirmation, calculating, by the computing device, the corrected relationship between the actual position of the reference marker and the portion of the patient's anatomy at the time, and re-register the reference marker with the portion of the patient's anatomy, wherein confirmation is received via a user interface associated with the computing device.

5. The method of claim 1, wherein the shift is due to an unintended disruptive contact of the reference marker during spine surgery, neurosurgery, or orthopedic surgery.

6. The method of claim 1, wherein the method is used during a spine surgery and the reference marker is positioned on a spinal process of the patient above an area of the spine undergoing the spine surgery and the at least one bump detection sensor is positioned on the spinal process of the patient.

7. The method of claim 1, further comprising: providing, by the computing device, a trajectory to an end effector of a stereotactic surgical robot associated with the computing device to at least assist with the surgical procedure being performed on the patient; and modifying, by the computing device, the trajectory in response to the automatic re-registration to include the corrected pose.

8. The method of claim 1, further comprising: displaying, by the computing device via a display device, at least one view of the portion of the patient's anatomy, the reference marker, or the at least one bump detection sensor, wherein outputting the corrected pose includes modifying the at least one view of the portion of the patient's anatomy, the reference marker, or the at least one dump detection sensor.

9. The method of claim 1, wherein the at least one bump detection sensor comprises a first bump detection sensor positioned on the portion of the patient's anatomy and at least a second bump detection sensor positioned on at least one of: a surgical table the patient is located on, an end effector of a stereotactic surgical robot working on the patient, or another portion of the patient's anatomy.

10. A navigation system comprising: a non-transitory memory storing instructions and data, including a static relationship between a position of at least one bump detection sensor and a position of a reference marker at an initial image registration time and a static relationship between the position of the reference marker and a position of a portion of the patient's anatomy at the initial image registration time, wherein the reference marker is configured to be positioned on the portion of the patient's anatomy and the at least one bump detection sensor; and a processor configured to access the memory to execute the instructions to at least: receive position data of an actual position of the reference marker at a time and an actual position of each of the at least one bump detection sensor at the time; determine a delta matrix based on the position data of the actual position of the reference marker at the time, the position data of the actual position of each of the at least one bump detection sensor at the time, and the static relationship between the positions of the at least one bump detection sensor and the reference marker at the initial image registration time; determine the shift in the actual position of the reference marker relative to the position of the anatomy at the time based on the delta matrix and the static relationship between the positions of the reference marker and the portion of the patient's anatomy at the initial image registration time; and determine whether automatic re-registration is required based on one or more predefined thresholds.

11. The navigation system of claim 10, wherein the navigation system is in communication with an imaging device configured to record data related to the at least one bump detection sensor marker and the reference marker.

12. The navigation system of claim 10, wherein the portion of the patient's anatomy is a rigid body and one of the at least one bump detection sensors is configured to be positioned on the rigid body adjacent to the reference marker.

13. The navigation system of claim 12, wherein at least a second bump detection sensor is configured to be positioned on a different rigid body than the reference marker.

14. The navigation system of claim 10, wherein the reference marker is configured to be positioned on a spinal process of the patient above an area of the spine being worked on by a user of the system; and wherein the at least one bump detection sensor is configured to be positioned on the spinal process of the patient.

15. The navigation system of claim 10, wherein the navigation system is in communication with a stereotactic surgical robot, and wherein the processor further comprises instructions to: provide a trajectory to an end effector of the stereotactic surgical robot, relative to a procedure; and modify the trajectory based on the automatic re-registration.

16. The navigation system of claim 10, further comprising an output device configured for image guided surgery and displaying at least one view of at least one of the portion of the patient's anatomy, the reference marker, and the at least one bump detection sensor.

17. The navigation system of claim 10, wherein the at least one bump detection sensor is an optical sensor, an accelerometer, a gyroscope, a magnetometer, a potentiometer, a Hall effect sensor, a linear variable displacement transducer, a strain gage, an ultrasonic sensor, an electromagnetic sensor, and/or a laser distance measurement sensor.

18. The navigation system of claim 10, wherein the at least one bump detection sensor comprises a first bump detection sensor configured to be positioned on the portion of the patient's anatomy and at least a second bump detection sensor configured to be positioned on at least one of: a surgical table the patient is located on, an end effector of a stereotactic surgical robot working on the patient, or another portion of the patient's anatomy.

19. The navigation system of claim 18, wherein the at least the second bump detection sensor is configured to detect robotic compliance and/or a robot positioning error in a robot associated with the navigation system.

20. The navigation system of claim 10, further comprising a surgical tool, wherein the automatic re-registration is based on the proximity of the surgical tool to the reference marker and the at least one bump detection sensor.

* * * * *